United States Patent [19]

Wissner

[11] 4,039,574

[45] Aug. 2, 1977

[54] 13-HYDROXY-15-DEOXY-PROSTAGLANDINS

[75] Inventor: Allan Wissner, Monsey, N.Y.

[73] Assignee: American Cyanamid Company, Stamford, Conn.

[21] Appl. No.: 616,514

[22] Filed: Sept. 25, 1975

[51] Int. Cl.$^2$ ............................................. C07C 177/00
[52] U.S. Cl. .......................... 260/514 D; 204/158 R; 260/410; 260/413; 260/468 D; 260/471 C; 260/471 A; 260/473 A; 260/473 G; 260/475 P; 260/476 R; 260/488 R; 260/514 J; 424/305; 424/317
[58] Field of Search ....................... 260/468 D, 514 D

[56] References Cited

U.S. PATENT DOCUMENTS 3,887,587  6/1975  Schaaf et al. ..................... 260/345.8

FOREIGN PATENT DOCUMENTS 155,442  10/1974  Czechoslovakia ................... 260/468

OTHER PUBLICATIONS

Greene et al., Tet. Letters, 937 (1975).

Primary Examiner—Robert Gerstl
Attorney, Agent, or Firm—Denis A. Polyn

[57] ABSTRACT

This disclosure describes 13-hydroxy-15-deoxy-prostaglandins which exhibit multiple biological responses even at low doses.

7 Claims, No Drawings

13-HYDROXY-15-DEOXY-PROSTAGLANDINS

BRIEF SUMMARY OF THE INVENTION

This invention relates to novel cyclopentanones having a prostaglandin like structure. These novel compounds may be represented by the following general formula:

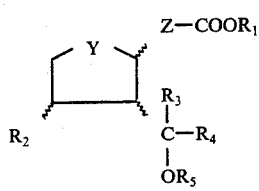

wherein $R_1$ is selected from the group consisting of hydrogen, straight of branched chain alkyl having up to 12 carbon atoms, cycloalkyl of from 3 to 10 carbon atoms, inclusive, phenyl, and phenyl substituted with up to 3 chlorine atoms, up to three alkyl groups each having up to 4 carbon atoms, hydroxy, carboxy or carboalkoxy having up to 3 carbon atoms, $R_2$ is selected from the group consisting of hydrogen, hydroxy, and alkanoyloxy having up to 4 carbon atoms; $R_3$ is selected from the group consisting of hydrogen and alkyl having up to 3 carbon atoms; $R_4$ is selected from the group consisting of hydrogen and straight or branched chain alkyl having up to 10 carbon atoms; $R_5$ is selected from the group consisting of hydrogen, alkanoyloxy having up to 8 carbon atoms, phenoxyacetyl in which the phenyl ring is optionally substituted with one or two substituents selected from the group consisting of halogen, alkyl having up to 3 carbon atoms, alkoxy having up to 3 carbon atoms, and trifluoromethyl, and phenyl substituted alkanoyl having up to 4 carbon atoms; the divalent radical Y is selected from the group consisting of those of the formulae:

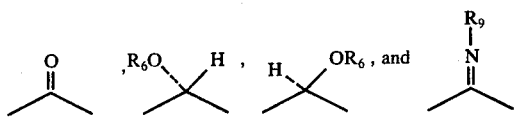

wherein $R_6$ is hydrogen or alkanoyl having up to 5 carbon atoms; $R_9$ is selected from the group consisting of hydroxy, alkoxy having up to 3 carbon atoms, ureido, thioureido, monoalkylamino or dialkylamino wherein alkyl has up to 4 carbon atoms, carboalkoxyamino having up to 3 carbon atoms, and anilino optionally substituted with one or two substituents selected from the group consisting of carboxy, carboxamido, halogen, alkyl having up to 3 carbon atoms, alkoxy having up to 3 carbon atoms, trifluoromethyl and mono- or di-alkylamino having up to 3 carbon atoms; $R_9$ can also be morpholino, piperazino, $N^4$-alkyl (up to 3 carbon atoms,) piperazino, $N^4$-phenylpiperazino, pyrrolidino, piperidino or homopiperidino, each of which may be optionally substituted with 1 or 2 alkyl groups having up to 3 carbon atoms; Z is a divalent radical selected from the group consisting of those of the formulae:

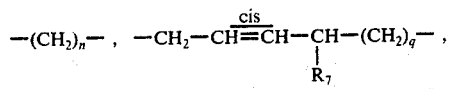

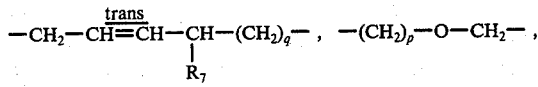

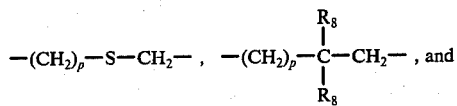

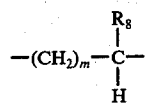

wherein $n$ is an integer from 4 to 8, inclusive; $q$ is an integer from 1 to 4, inclusive; $p$ is an integer from 2 to 6, inclusive; $m$ is an integer from 3 to 7, inclusive; $R_7$ is selected from the group consisting of hydrogen and alkyl having up to 3 carbon atoms, with the proviso that when Z is

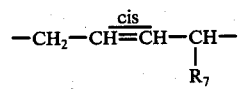

or 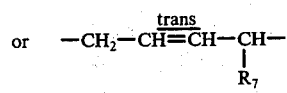

then $R_2$ is hydroxy or alkanoyloxy; and $R_8$ is alkyl having up to 3 carbon atoms, the moiety

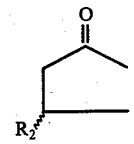

may be the divalent radical

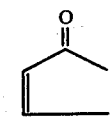

and the bonds indicated by ~ are taken to embrace both possible configurations.

Also embraced within the scope of the present invention are the useful pharmocologically acceptable salts of the above general formula, wherein $R_1$ is hydrogen, with pharmacologically acceptable metal cations, ammonium, amine cations, or quaternary ammonium cations. Especially preferred metal cations are those derived from the alkali metals, e.g., lithium, sodium and potassium, and form the alkaline earth metals, e.g., magnesium and calcium although cationic forms of other metals, e.g., aluminium, zinc, and iron, are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethyleneamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(P-tert-amylphenyl)diethanolamine, galactamine, N-methylglucamine, N-methylglucosamine, ephedrine, phenylephrine, epinephrine, procaine, and the like. Examples of suitable pharmacologically acceptable quarternary ammonium cations are tetramethylammonium, tetraethylammonium, benzyltrimethylammonium, phenyltriethylammonium, and the like.

The compounds of this invention are administered in various ways for various purposes, e.g., intravenously, intramuscularly, subcutaneously, orally, intravaginally, rectally, buccally, sublingually, topically and in the form of sterile implants for prolonged action. For intravenous injection or infusion, sterile aqueous isotonic solutions are preferred. For that purpose, it is preferred because of increased water solubility that $R_1$ be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixers, and simple solutions, with the usual pharmaceutical carriers are used for oral or sublingual administration. For rectal or vaginal administration, suppositories prepared as known in the art are used. For tissue implants, a sterile tablet or silicone rubber capsule or other object containing or impregnated with the substance is used. On certain occasions it may be advantageous to administer the compounds of this invention as clathrate compounds with substances such as $\beta$-cyclodextrin.

DETAILED DESCRIPTION OF THE INVENTION

The prostaglandins are a family of closely related compounds which have been obtained for various animal tissues, and which stimulate smooth muscle, lower arterial blood pressure, antagonize epinephrine-induced mobilization of free fatty acids, and have other pharmacological and autopharmacological effects in mammals. See Bergstrom et al., J. Biol. Chem. 238, 3555 (1963) and Horton, Experienta 21, 113 (1965) and references cited therein. All of the so-called natural prostaglandins are derivatives of prostanoic acid:

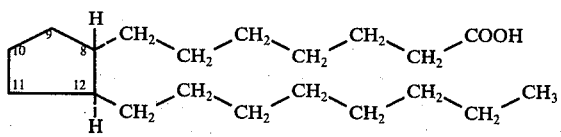

The hydrogen atoms attached to C-8 and C-12 are in trans-configuration. When the hydrogen atoms attached to C-8 and C-12 are in a cis relationship, the iso-prostanoic acid skeleton is obtained as follows:

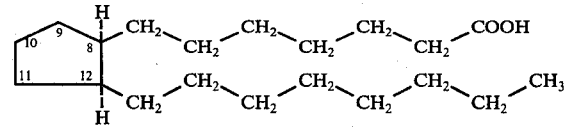

In drawing these structures a dotted line connecting a ring carbon atoms to a side chain is used to indicate that the side chain is below the plane of the paper and is said to have a $\alpha$ configuration. A solid line connecting a ring carbon and a side chain denotes that it is above the plane of the paper and is said to have a $\beta$ configuration. Unless noted otherwise, structural formulae used in this description represent all possible optical isomers. The compounds described in this invention include the derivatives of prostanoic acid and of iso-prostanoic acid as well as all their possible optical isomers. The novel cyclopentanones of this invention may be prepared from certain substituted cyclopentenones (I), whose preparation has been previously disclosed (Netherlands Pat. Nos. 7310-276 and 7310-277, both issued Jan. 28, 1974; see Derwent Central Patents Index, Basic Abstracts Journal, 13-Farmdoc, 10735 V/06 and 10736 V/06, respectively.), as shown in Flowsheet A.

FLOWSHEET A

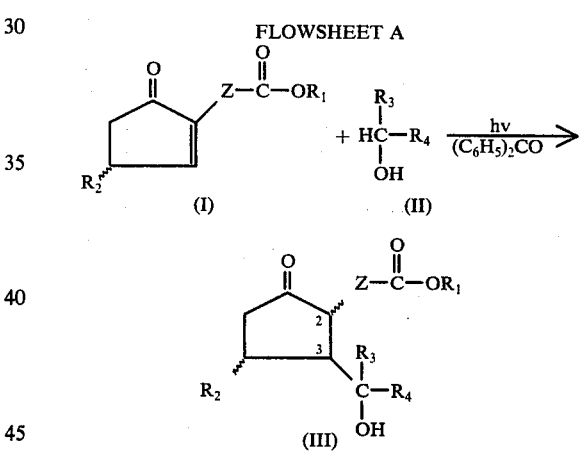

In Flowsheet A above, $R_1$, $R_2$, Z, $R_3$, and $R_4$ are as hereinabove defined. As shown in this scheme, the cyclopentenones are irradiated in the presence of primary or secondary alcohols (II) which usually also serve as the solvent. The irradiations are conducted in Pyrex vessels under a nitrogen atmosphere using benzophenone as a sensitizer and a 350 mu light source. The products (III) are obtained as mixtures of isomers which, if desired, can be separated into component isomers using chromatographic techniques which may include if necessary multiple passes through a high pressure liquid chromatograph [see G. Fallick, American Laboratory 19-27 (August, 1973)]. In some cases, it is possible to treat the mixture of isomers with bases such as potassium carbonate, potassium acetate, and sodium hydroxide which will epimerize any of the isomers containing the groups at C-2 and C-3 in a cis relationship to the corresponding isomer in which the group at C-2 and C-3 are in a trans relationship.

In Flowsheet B is shown how the novel cyclopentenones (VI) embraced in this invention are prepared.

FLOWSHEET B

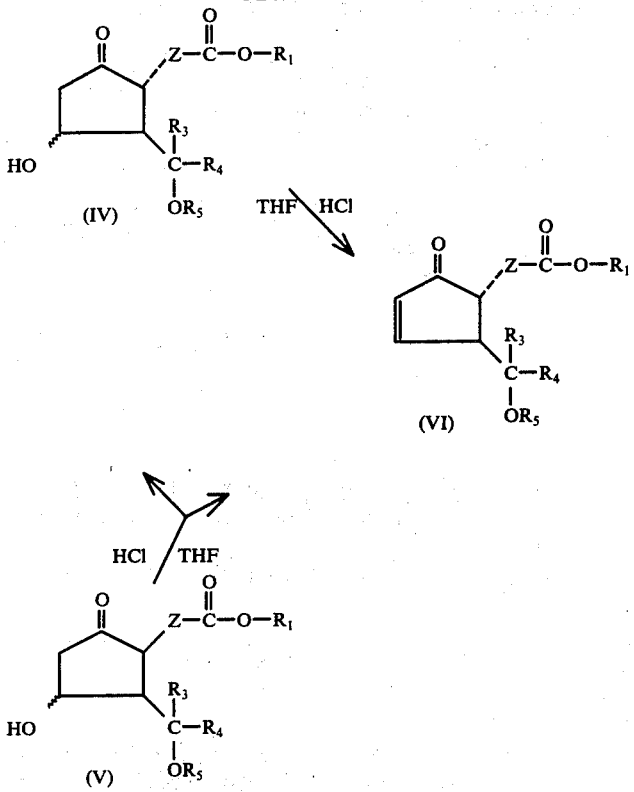

In Flowsheet B above $R_1$, $R_3$, $R_4$, $R_5$ and Z are as hereinabove defined. As indicated in the above scheme, treatment of the hydroxycyclopentanones (IV) in which there is a trans relationship between the chains at C-2 and C-3 with dilute hydrochloric acid in tetrahydrofuran gives the cyclopentenones (VI) with a trans relationship between the chains. Treatment of the hydroxycyclopentanones (V) in which there is a cis relationship between the chains at C-2 and C-3 under the same conditions gives the same cyclopentenones (VI) with trans chains. Moreover, under these reaction conditions the hydroxycyclopentanones with the cis chains (V) are epimerized to the hydroxycyclopentanones with the trans chains (IV) at the same time as the cyclopentanones (VI) are forming. This accounts for the formation of cyclopentenones (VI) with trans chains from hydroxycyclopentanones (V) with cis chains. In those cases where $R_3$ and $R_4$ in the cyclopentanones (VI) are different, there are two possible isomers which differ in configuration at the carbon containing the —$OR_5$ group. These isomers can, if desired, be separated by various chromatographic techniques which may include if necessary multiple passes through a high pressure liquid chromatograph.

The preparation of the novel cyclopentanols claimed in this invention is shown in Flowsheet C.

FLOWSHEET C

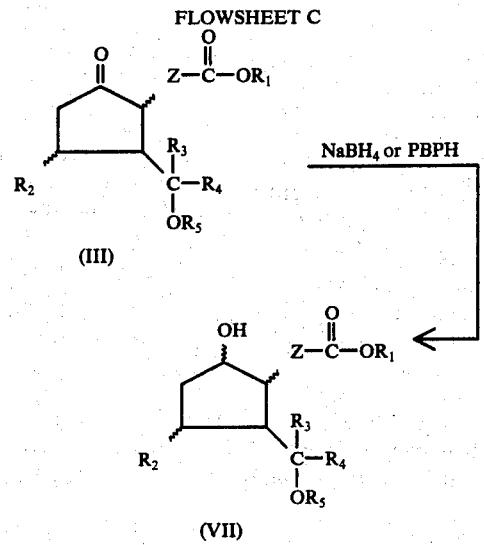

wherein $R_1$, $R_2$, $R_3$, $R_4$, $R_5$ and Z are as hereinabove defined. As shown in the above scheme, the cyclopentanones (III) can be reduced either as the isomer mixture or as the separated isomers using sodium borohydride in ethanol or lithium perhydro-9b-boraphenalylhydride (PBPH) in tetrahydrofuran to give the cyclopentanols (VII). In those cases where the cyclopentanols (VII) are obtained as mixtures of isomers, the isomers can be separated, if desired, by various chromatographic techniques which may include if necessary multiple passes through a high pressure liquid chromatograph.

Esterification of the carboxylate group in the compounds described in this invention is accomplished as shown in Flowsheet D.

FLOWSHEET D

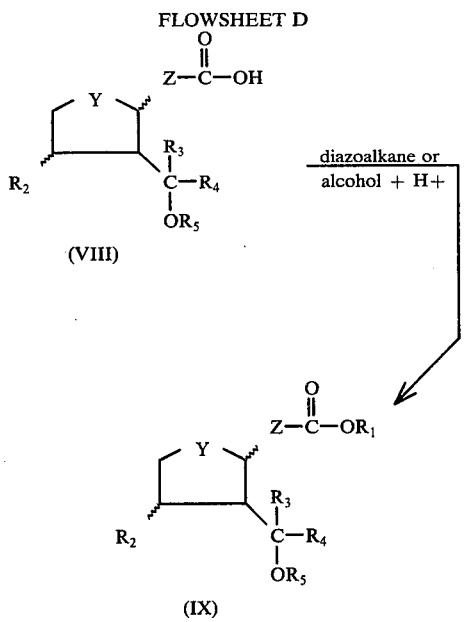

(VIII)

(IX)

In Flowsheet D above $R_1$, $R_2$, $R_3$, $R_4$, $R_5$ and Z are as hereinabove defined. As shown in Flowsheet D the reaction of the acids (VIII) with an etheral solution of the desired diazoalkane gives the corresponding ester (IX). In those cases where $R_2$ is hydrogen, esters can also be prepared by heating the acid with the desired alcohol and catalytic amount of sulfuric acid. It should be pointed out that these esters can also be prepared directly from the appropriate cyclopentanone ester I as shown in Flowsheet A. The preparation of diazoalkanes by various procedures are well described in the art, see for example C. D. Gutsche *Organic Reactions,* VIII, 389 (1954). The various esters can also be prepared by any of several procedures well-known in the art via an acid chloride (prior blocking of free alcohl groups with appropriate blocking groups such as trialkylsilyl, tetrahydropyranyl and the like) or mixed mixed anhydride and treatment of these intermediates with the appropriate alcohol. Mixed anhydrides can be obtained by treatment of the progstaglandin acid in a solvent such as dioxane at a temperature in the range 0° to 15° C. with a molar equivalent of a tri-alkylamine, preferably triethylamine, tributylamine and the like, and then a molar equivalent of isobutyl chlorocarbonate or the like. The resulting mixed anhydride is then treated with the appropriate alcohol to give the derivatized product. (For a pertinent literature analogy see *Prostaglandins,* 4, 738 (1973).

An alternative procedure for the preparation of esters involves treatment of the prostaglandin acid with a molar equivalent of the trialkyl amine in an excess of the appropriate alcohol in an anhydrous solvent such as methylene chloride, one or if necessary 2 molar equivalents of p-toluenesulfonyl chloride are then added and after stirring at ambient temperatures for about 15 minutes to 1 hour the product is worked up in the usual way, (For pertinent literature analogy see U.S. Pat. No. 3,821,279, June 28, 1974.) A third procedure involves use of dicyclohexylcarbodiimide in the usual manner; for a pertinent literature analogy see German Offen. No. 2,365,205 (July 11, 1974); *Chem. Abst.,* 81, 120098 g. (1974).

As shown in Flowsheet E below, wherein $R_1$, $R_3$, $R_4$, $R_5$ and Z are as hereinabove defined, alkanoylation of the side chain hydroxyl groups in (X) can be accomplished by the reaction with the desired acid chloride or anhydride to give the desired esters (XI).

FLOWSHEET E

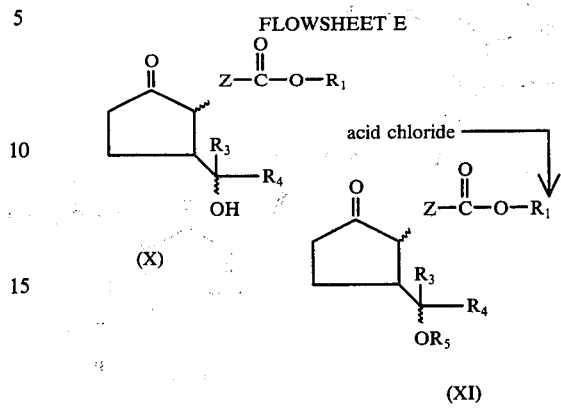

(X)

(XI)

Moreover, the other esters claimed in this invention can be prepared using similar techniques as those described above.

The preparation of those compounds for which Z is $$-CH_2-\overset{trans}{CH=CH}-\underset{R_7}{CH}-(CH_2)_q-$$

wherein $R_7$ and $q$ are as hereinabove defined is accomplished by irradiation of the corresponding cis compound wherein Z is $$-CH_2-\overset{cis}{CH=CH}-\underset{R_7}{CH}-(CH_2)_q-$$

in an oxygen free benzene-methanol solution in the presence of diphenylsulfide using a 3500A light source. For a pertinent literature analogy see G. L. Bundy et al., *J. Amer. Chem. Soc.,* 94, 2124 (1972) and U.S. Pat. No. 3,821,291 (June 28, 1974).

By using the procedure outlined in Flowsheet A, it is also possible to prepare individual enantiomers of (III) ($R_2$ is not hydrogen) by photochemical addition of alcohols to the resolved 4-hydroxycyclopentenones (XIII and XIV) in which case (III) is obtained as a mixture of isomers each of which is optically active. The individual enantiometer can then be obtained by chromatographic procedures using, if necessary, multiple high pressure liquid chromatographic procedures.

The 4-hydroxycyclopentenone racemates may be resolved into their component enantiomers (XIII) and (XIV) by derivatizing the ketone function with a reagent having an optically active center. The resulting diastereomeric mixture can then be separated by fractional crystallization, or by chromatography, or by high speed liquid chromatography involving, if necessary, recycling techniques. Among the useful optically active ketone derivatizing reagents are 1-α-aminoxy-γ-methylpentanoic acid hydrochloride (to give (XV), (R)-2-aminoxy-3,3-dimethylbutyric acid hydrochloride, and 4-α-methylbenzyl semicarbazide. After separation of the diastereomeric derivatives, reconstitution of the keto function provides the individual 4-hydroxycyclopentenone enantiomers (XIII) and (XIV). A useful procedure for the resolution of a 4-hydroxycyclopentenone racemate via an oxime such as (XV) is described in the art [R. Pappo, P. Collins and C. Jung, *Tetrahedron Letters*, 943 (1973)].

2627 (1972) and R. Pappo, P. Collins and C. Jung, *Ann. N.Y. Acad. Sci.*, 180, 64 (1971). For a descriptive of the baker's yeast procedure see C. J. Sih et al., *Journ. Amer. Chem. Soc.*, 94 3643 (1972); 97, 857 (1975).

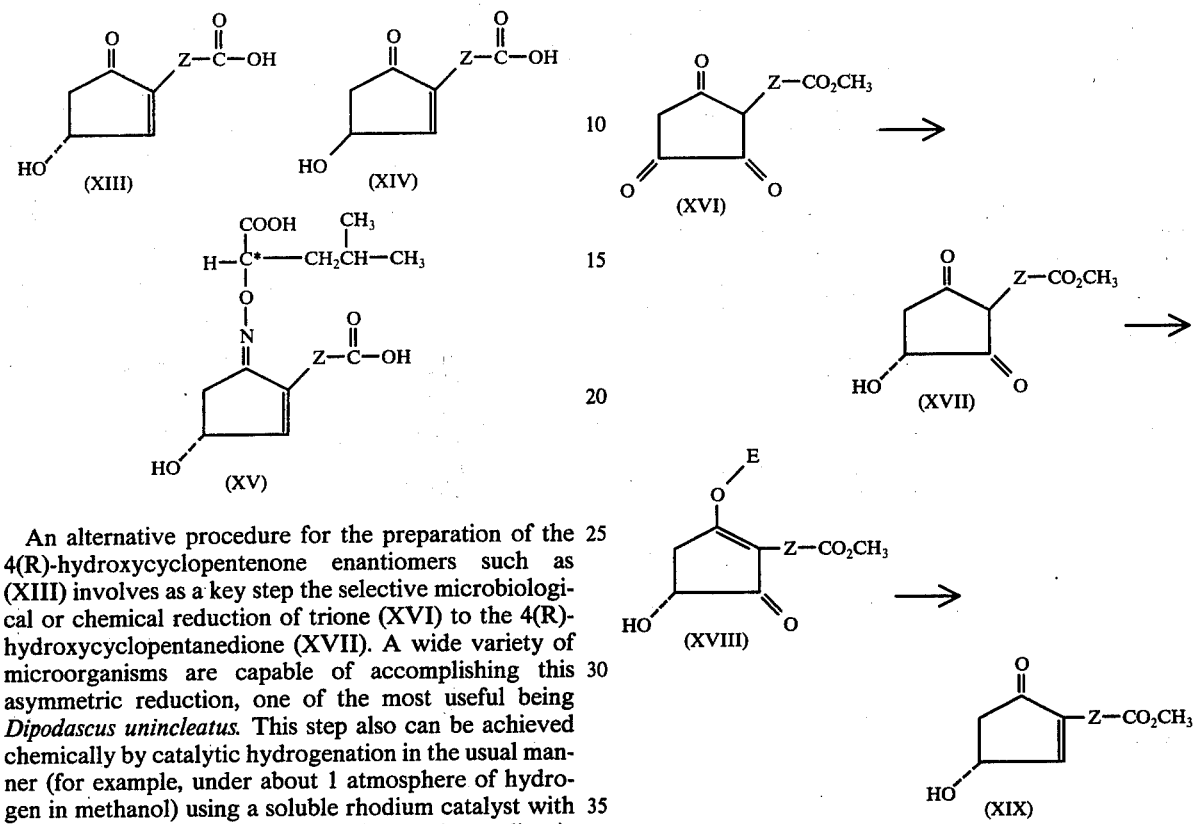

An alternative procedure for the preparation of the 4(R)-hydroxycyclopentenone enantiomers such as (XIII) involves as a key step the selective microbiological or chemical reduction of trione (XVI) to the 4(R)-hydroxycyclopentanedione (XVII). A wide variety of microorganisms are capable of accomplishing this asymmetric reduction, one of the most useful being *Dipodascus unincleatus*. This step also can be achieved chemically by catalytic hydrogenation in the usual manner (for example, under about 1 atmosphere of hydrogen in methanol) using a soluble rhodium catalyst with chiral phosphine ligands, such as (1,5-cyclooctadiene)-bis(o-anisylcyclohexylmethylphosphine)rhodium (I) tetrafluoroborate in the presence of one equivalent of organic base, such as triethylamine.

Conversion of hydroxycyclopentanedione (XVII) to an enol ether or enol ester, (XVIII, E = alkyl, preferably isopropyl; aroyl such as benzoyl; or arylsulfonyl such as 2-mesitylenesulfonyl), is accomplished by treatment, for example, with isopropyl iodide and a base such as potassium carbonate in refluxing acetone for from 15 to 20 hours, or with a base such as triethylamine and 0.95 equivalents of benzoyl chloride or a slight excess of 2-mesitylenesulfonyl chloride, in a non-prototropic solvent at a temperature of about −10° to −15° C. Reduction of (XVIII) with excess sodium bis(2-methoxyethoxy) aluminum hydride in a solvent such as tetrahydrofuran or toluene at low temperatures, such as −60° to −78° C., followed by mild acid hydrolysis (representative conditions: aqueous dilute hydrochloric acid, pH 2.5; or oxalic acid, sodium oxalate in chloroform) at ambient temperatures from 1 to 3 hours provides the 4(R)-hydroxycyclopentenone ester (XIX). The ester (XIX) can be subjected to photochemical addition reactions as described hereinabove. The photochemical addition product will then be a methyl ester which can be hydrolyzed to the corresponding carboxylic acid by enzymatic or microbiological procedures, for example with baker's yeast or by exposure to *Rhizopus oryzae*.

For a description of these procedures in the art see: C. J. Sih et al., *Journ. Amer. Chem. Soc.*, 95 1676 (1973); 97, 865 (1975); J. B. Heather et al., *Tetrahedron Letters*, 2213 (1973); R. Pappo and P. W. Collins, *Tetrahedron Letters*, Procedures for the preparation of the requisite cyclopentanetriones (XVI) are well-established in the art and generally involve the treatment of an ω-1-oxo long chain ester (XX) with methyl or ethyl oxalate and a base such as sodium methoxide in methanol, followed by treatment with dilute hydrochloric acid in aqueous methanol to effect the dealkoxalylation of the intermediate (XXI). See J. Kutsube and M. Matsui, *Agr. Biol. Chem.*, 33, 1078 (1969); P. Collins, C. J. Jung and R. Pappo, *Israel Journal of Chemistry*, 6, 839 (1968); R. Pappo, P. Collins and C. Jung, *Ann. N.Y. Acad. Sci.* 180, 64 (1971); C. J. Sih et al., *Journ. Amer. Chem. Soc.*, 95, 1676 (1973) (see reference 7); and J. B. Heather et al., *Tetrahedron Letters*, 2313 (1973) for pertinent background Literature.

$$CH_3-\overset{O}{\overset{\|}{C}}-CH_2-Z-CO_2CH_3$$

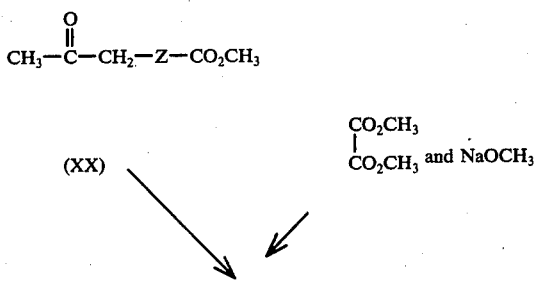

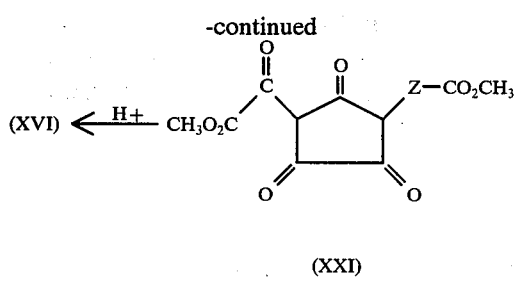

(XXI)

The intermediate keto esters (XX) may be prepared by a variety of methods known to the art. One useful procedure is outlined below and involves alkylation of ethyl acetoacetate sodium salt (XXII) in the usual manner with the appropriate side-chain precursor (XXIII, X=Cl, Br, I, preferably Br or I) followed by decarbethoxylation and reesterification, all in the usual manner.

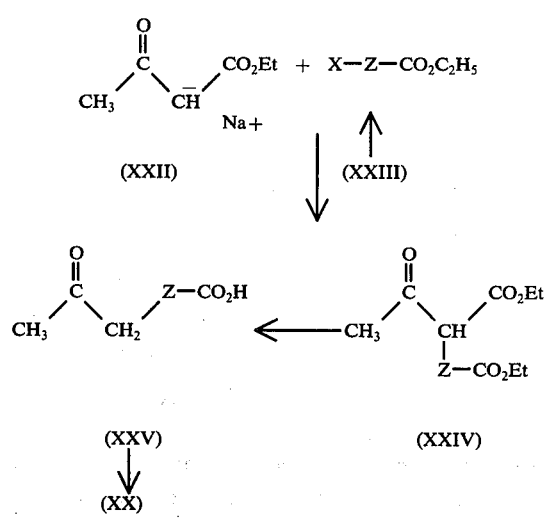

The side-chain precursors (XXIII) are commercially available where Z is —$(CH_2)_n$— and can be prepared as described in Belgian Pat. No. 786,215 (granted and opened to inspection Jan. 15, 1973) where Z is

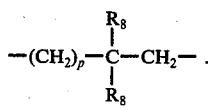

Where Z is

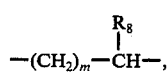

precursor (XXIII) can be prepared as indicated below by mono-tetrahydropyranylation of the diol (XXVI) to (XXVII), followed by mesylation, treatment of the resulting mesylate (XXVIII) with the appropriately substituted sodium malonate to give (XXIX), decarbethoxylation and reesterification to (XXX), mesylation of the second hydroxy function to (XXXI) and displacement with lithium bromide (or iodide) to (XXXII). Alternatively, the ω-bromo alcohol (XXXIII) after blocking as the tetrahydropyranyl derivative (XXXIV), on treatment with the substituted sodio malonate provides (XXIX).

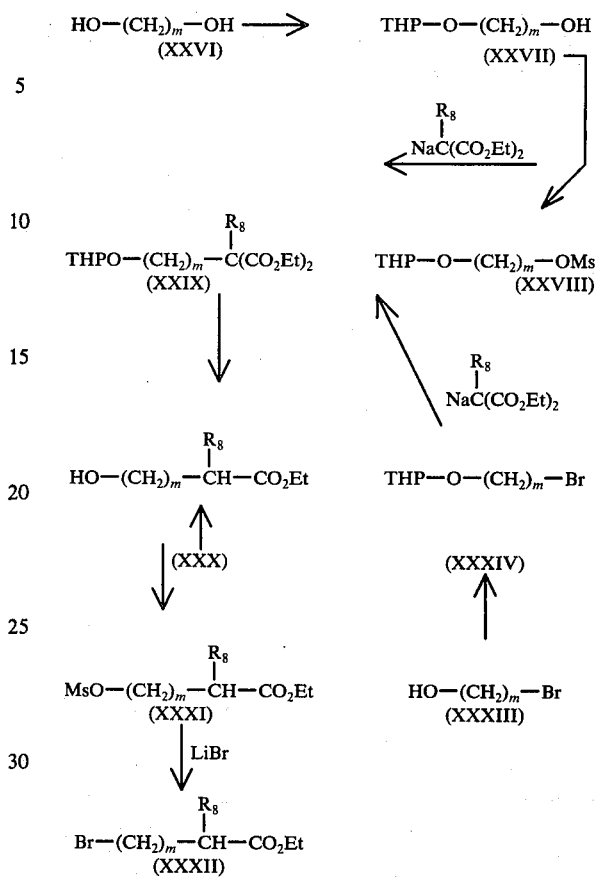

Those precursors wherein Z is —$(CH_2)_p$—O—$CH_2$— can be prepared by the transformation shown directly below starting with the mono-tetrahydropyranyl derivative (XXVII). Thus, (XXVII) is converted to the lithium alcoholate by treatment with butyl lithium, the alcoholate is then O-alkylated with ethyl bromoacetate to provide (XXXIV), which on de-tetrahydropyranylation, mesylation and reaction with lithium bromide gives the required (XXXVII). (These and all the above-described transformation can be effected in the usual manner, well-established in the art; pertinent examples for most of the reactions can be found in the above-cited Belgian Pat. No. 786,215.)

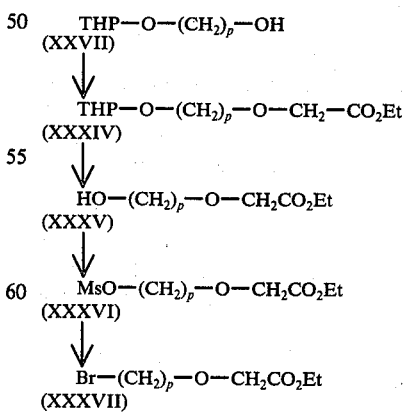

It is also possible to resolve the 4-hydroxycyclopentenone racemate (XXXVIII) by microbiological means. Thus, treatment of the 4-O-alkanoyl or aroyl derivatives (XXXIX, $R_{14}$ = aryl or alkyl) of racemate (XXXVIII) (preferably the 4-O-acetyl and 4-O-propionyl derivatives) with an appropriate microorganism preferably a Saccharomyces species, e.g. 1375-143, affords preferantial de-O-acylation of the 4(R)-enantiomer to give (XIII), which is then separated from the unreacted 4(S)-O-acyl enantiomer (XL) by chromatographic procedures. After separation, mild hydrolysis of the 4(S) derivative (XL) provides the 4(S)-hydroxycyclopentenone (XIV) [See N. J. Marscheck and M. Miyano, *Biochimica et Biophysica Acta*, 316, 363 (1973) for related examples.]

(XLII) wherein $R''_1$ is hydrogen or an alkoxy group, $n'$ is zero or two and Z is as hereinabove defined.

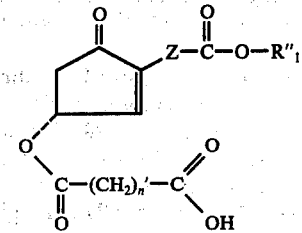

(XLII)

(XXXVIII)        (XXXIX)

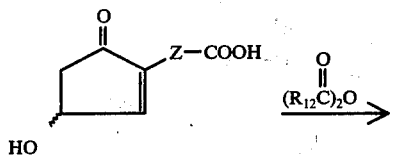 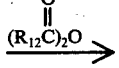 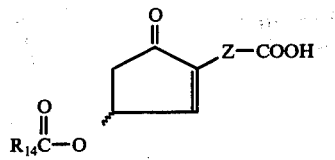

(XIII)        (XL)

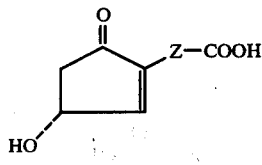    +    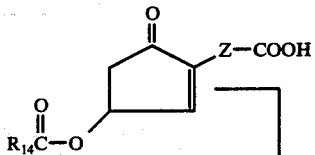

(XIV)

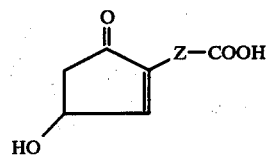

It is also possible to prepare the individual 4-hydroxycyclopentenones (XIII) and (XIV) directly by selective microbial hydroxylation of the corresponding 4-unsubstituted cyclopentenone (XLI). For example, with *Aspergillus niger* ATCC 9142, a selective 4(R)-hydroxylation of (XLI) [Z = $(CH_2)_6$] has been reported; for a literature example, see S. Kurozumi, T. Tora and S. Ishimoto, *Tetrahedron Letters*, 4959 (1973). Other organisms can also accomplish this hydroxylation.

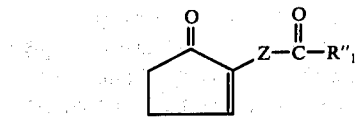

(XLI)

An alternate resolution procedure involves derivatization of the alcohol function of the racemic hydroxycyclopentenone to give ester-acid derivatives such as Such derivatives may be obtained from the corresponding free hydroxycyclopentenone by treatment in the usual manner with oxalyl chloride, succinyl chloride, succinic anhydride and the like. Treatment of the resulting acid or diacid ($R''_1$ = hydrogen) with optically active amines e.g., 1-(−)-α-methylbenzylamino, d-(+)-α-methylbenzylamine, brucine, dehydroabietylamine, strychnine, quinine, cinchonine, quinidine, ephedrine, (+)-α-amino-1-butanol and the like, and fractional recrystallization of the resulting diastereomeric mixtures, followed by cleavage of the 4-oxy ester function in each of the individually isolated diastereomers provides the individual 4(S)- and 4(R)-hydroxycyclopentenone enantiomers (XIII) and (XIV) or their respective esters. Cleavage of the oxalate acid ester (XLII, $n = 0$) can be accomplished by treatment with lead tetraacetate in pyridine solution. For an example of a similar use of oxalate acid-esters see J. G. Molotkovsky and L. D. Bergelson, *Tetrahedron Letters*, 4791 (No. 50, 1971); for an example of the use of succinate acid-ester see B. Goffinet, Ger. Offen. 2,263,880; *Chem. Abstracts*, 79, 78215$_z$ (1973).

For the preparation of the resolved enantiomers of (III) in those cases where $R_2$ is hydrogen (XLIII) the methods described below are useful. As described above in Flowsheet C, reduction of cyclopentanones (III) with hindered reducing agents such as lithium perhydro-9b-boraphenalylhydride (PBPH) gives the cyclopentanols (VII); moreover for the cyclopentanones (XLIII) of this invention, reduction with PBPH leads to two diastereomeric racemates (XLIV and XLV $R_3 \neq R_4$; when $R_3 = R_4$ only one racemate is formed) in both of which the new hydroxy group has an α-configuration (i.e. the hydroxy group and the chain

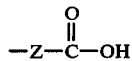

are cis).

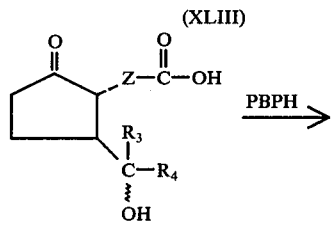

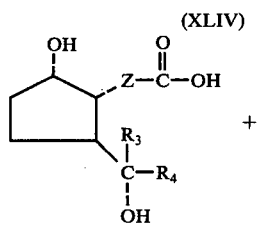

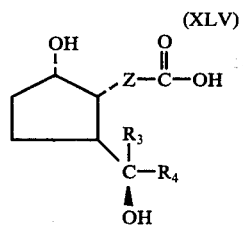

It is possible to separate (XLIV) and (XLV) by chromatographic procedures well known to the art. Both (XLIV) and (XLV) moreover can be resolved into their component enantiomers; this will be illustrated for (XLIV), it being understood that, (XLV) can be resolved in a like manner.

One procedure involves conversion of racemate (XLIV), wherein the chain hydroxy function has been preferentially blocked by a tetrahydropyranyl or trialkylsilyl group, to the corresponding phthalate half acid-ester, deblocking the chain hydroxy function and conversion of the diacid (e.g., XLVI) to a bis salt (e.g., XLVII) with an optically active amine (e.g., 1-(−)-α-methylbenzylamine, D-(+)-α-methylbenzylamine, brucine, dehydroabietylamine, strychnine, quinine, cinchonine, cinchonindine, quinidine, ephedrine, deoxyephedrine, amphetamine, (+)-2-amino-1-butanol, (−)-2-amino-1-butanol and the like). The resulting diastereomers (XLVII) are separated by fractional crystallization and the individual components are then converted by acidification and saponification to (XLVIII) and (IL), oxidation of which, after preferential blocking of the chain hydroxy function with a tetrahydropyranyl or trialkylsilyl group, provides the corresponding individual enantiomers (L) and (LI), after deblocking of the hydroxyl group. (For an appropriate literature procedure see E. W. Yankee, C. H. Lin and J. Fried, *Journ. Chem. Soc.*, 1972, 1120).

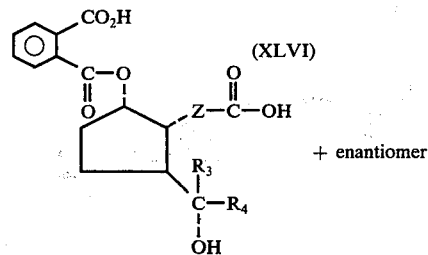

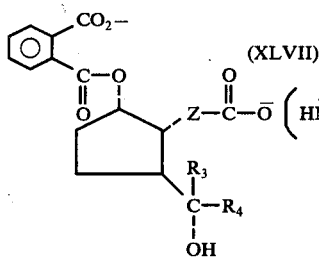

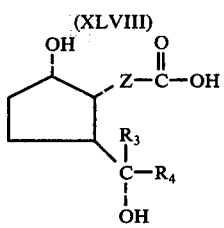 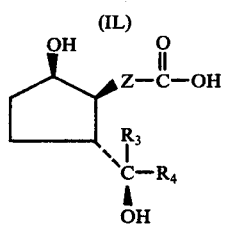

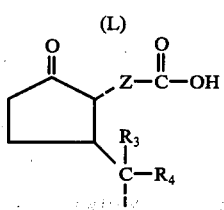 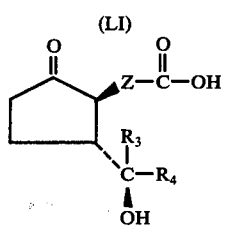

Another procedure involves conversion of the racemate (XLIV) (as the acid ester and with the chain alcohol function preferentially blocked as a tetrahydropyranyl or trialkylsilyl ether) to the diastereomeric carbamates with an optically active isocyanate, e.g., (+)-1-phenylethylisocyanate or (−)-1-phenylethylisocyanate, followed by deblocking. Separation of the diastereomers, for example (LII) and (LIII), can be accomplished by fractional crystallization or by the usual chromatographic procedures, or if necessary by high speed liquid chromatography involving, if necessary, recycling techniques. Base-treatment of the individual diastereomeric carbamates affords the individual enantiomeric alcohols, for example (XLVIII) and (IL).

(LII)

-continued

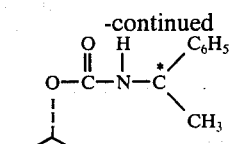

(LIII)

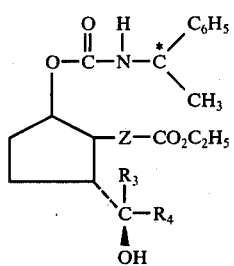

It is also possible to effect resolution of the racemate (XLIV), preferably as an ester, by esterification of the hydroxy function (prior preferential blocking of the chain hydroxy function as a tetrahydropyranyl or trialkylsilyl ether) with an optically active acid, via its acid chloride, followed by deblocking the chain alcohol group. Suitable optically active acids include ω-camphoric acid, menthoxyacetic acid, 3α-acetoxy-Δ⁵-etianic acid, (—)-α-methoxy-α-trifluoromethylphenylacetic acid and (+)-α-methoxy-α-trifluoromethylphenylacetic acid, and the like. The resulting diastereomeric esters, for example (LIV) and (LV), are then separated by fractional crystallization or by chromatographic techniques including, if necessary, the use of high speed liquid chromatography. Saponification of the individual diastereomers then provides the individual enantiomers (XLVIII) and (IL).

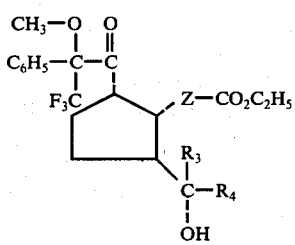

(LIV)

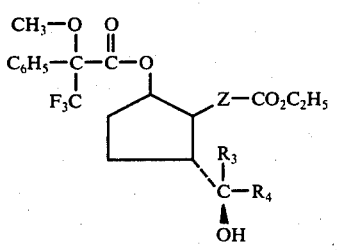

(LV)

Another resolution involves derivatization of the keto function of a racemic cyclopentanone acid or ester to give diastereomers (LVI) and (LVII), for example, with the usual type of ketone derivatizing agents bearing an optically active center. The resulting mixture of diastereomeric derivatives can then be separated by fractional crystallization or by chromatography or, if necessary, by high speed liquid chromatography. The individual diastereomeric keto derivatives, for example, (LVI) and (LVII), are then convertable to the individual cyclopentanone (LVIII) and (LVIX) by any of the usual cleavage techniques. Among the optically active reagents useful for ketone derivatization are 1-α-aminoxy-α-methylpentanoic acid hydrochloride [E. Testa et al., Helv. Acta, 47 (3), 766 (1973)], menthylhydrazine, and 4-α-methylbenzylsemicarbazide. A useful procedure for the cleavage of oximes such as (LVI) and (LVII) involves treatment of the oxime at about 60° C. for about 4 hours in 1:2 aqueous-tetrahydrofuran buffered with ammonium acetate and containing titanium trichloride.

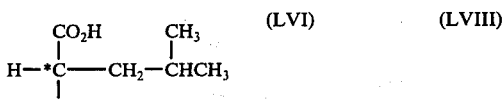

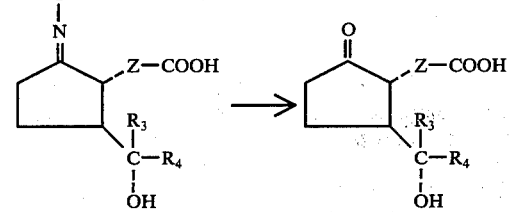

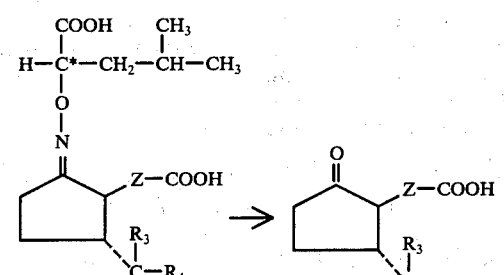

Other useful ketone derivatizing agents are optically active 1,2-glycols, e.g., D(—)-2,3-butanediol, or 1,2-dithiols, e.g., L(+)-2,3-butanedithiol. These are used to convert the cyclopentanones to alkylenedioxa or alkylenedithia derivatives, separation of diastereomers by chromatographic procedures followed by regeneration of the individual cyclopentenone enantiomers by ketal cleavage all by procedures well-known in the art.

In referring to the structures of the compounds of this invention, the terms α and β refer to the fact that a substituent is below and above the plane of the paper. For example, in the structure shown below R' and R''' are α while R'' is β.

The ring system of certain of the novel compounds of this invention allow them to be characterized as follows:

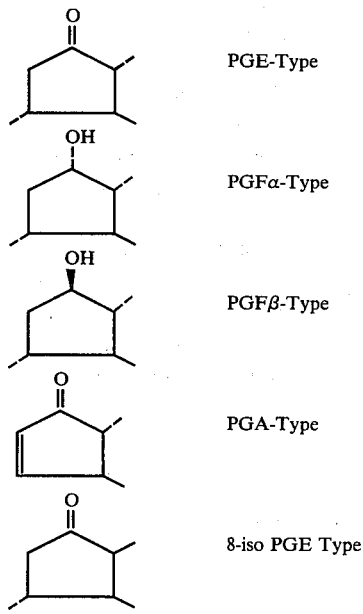

PGE-Type

PGFα-Type

PGFβ-Type

PGA-Type 8-iso PGE Type

The novel compounds of this invention possess the pharmacological activity described below as associated with the appropriate above-described prostaglandin type.

The known PGE, PGFα, PGFβ, and PGA compounds are all potent in causing multiple biological responses even at low doses. For example, PGE₁ and PGE₂ are extremely potent in causing vasodepression and smooth muscle stimulation, and also are potent as antilipolytic agents. Moreover, for many applications, these known prostaglandins have an inconveniently short duration of biological activity. In striking contrast, the novel prostaglandin analogs of this invention are substantially more specific with regard to potency in causing prostaglandin-like biological responses, and/or having a substantially, longer duration of biological activity. Therefore, each of these novel prostaglandins analogs is surprisingly and unexpectedly more useful than one of the corresponding above-mentioned known prostaglandins for at least one of the pharmacological purposes indicated below for the latter, either because it has a different and narrower spectrum of biological activity than the known prostaglandins, and therefore is more specific in its activity and causes smaller and fewer undesired side effects than the known prostaglandins, or because of its prolonged activity, fewer and smaller doses of the novel prostaglandin analog can frequently be used to attain the desired result.

The 11-deoxy-PGE, PGFα and PGFβ compounds are additionally selective in that they are at most relatively very weak stimulants of smooth muscle. The 11-deoxy PGE compounds have a further advantage in that they are as much more stable and have a longer "shelf-life" than the corresponding 11-hydroxy derivatives as described more fully hereinbelow.

Another advantage of the novel compounds of this invention, compared with the known prostaglandins, is that these novel compounds are administered effectively, orally, sublingually, intravaginally, bucally, or rectally, in addition to the usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

PGE₁, PGE₂, PGE₃, and dihydro-PGE₁, and the corresponding PGFα, PGFβ, and PGA compounds, and their esters and pharmacologically acceptable salts, are extremely potent in causing various biological responses. For that reason, these compounds are useful for pharmacological purposes. See, for example, Bergstrom et al., Pharmacol. Rev. 20, 1 (1968), and references cited therein. A few of those biological responses are systemic arterial blood pressure lowering in the case of the PGE, and PGFβ and PGA compounds as measured, for example, in anesthetized (phenobarbital sodium) pentolinium-treated rats with indwelling aortic and right heart cannulas; pressor activity, similarly measured, for the PGFα compounds; stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion; activity on the central nervous system; decrease of blood platelet adhesiveness in the case of PGE, as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the PGE compounds, stimulation of epidermal proliferation and keratinization as shown when applied in culture to embryonic chick and rat skin segments.

Because of these biological responses, these known prostaglandins are useful to study, prevent, control, or alleviate a wide variety of disease and undesirable physiological conditions in birds and mammals, including humans, usefully domestic animals, pets, and zoological specimens, and in laboratory animals, for example, mice, rats, rabbits, and monkeys.

For example, these compounds, and especially the PGE compounds, are useful in mammals, including man, as nasal decongestants. For this purpose, the compounds are used in a dose range of about 10 μg. to about 10 mg. per ml. of a pharmacologically suitable liquid vehicle or as an aerosol spray, both for topical application.

The PGE and PGA compounds are useful in mammals, including man and certain useful animals, e.g., dogs and pigs, to reduce and control excessive gastric secretion, thereby reducing or avoiding gastric erosion or gastrointestinal ulcer formation, and accelerating the healing of such ulcers already present in the gastrointestinal tract. For this purpose, the compounds are injected or infused intravenously, subcutaneously, or intramuscularly in the infusion dose range about 0.1 to about 500 μg. per kg. of body weight per minute, or in a total daily dose by injection or infusion in the range about 0.1 to about 20 mg. per kg. of body weight per day, the exact dose depending on the age, weight, and condition of the patient or animal, and on the frequency and route or administration. These compounds may also be useful in conjunction with various non-steroidal anti-inflammatory agents, such as aspirin, phenylbutazone, indomethacin and the like, to minimize the well-known ulcerogenic effects of the latter.

The PGE$_1$ compounds are useful whenever it is desired to inhibit platelet aggregation, to reduce the adhesive character of platelets, and to remove or prevent the formation of thrombi in mammals, including man, rabbits, and rats. For example, these compounds are useful in treatment and prevention of myocardial infarcts, to treat and prevent post-operative thrombosis. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range of about 0.005 to about 20 mg. per kg. of body weight per day are used, the exact dose depending on the age, weight, and condition of the patient or animal, and on the frequency and route of administration.

11α-Hydroxy-PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore PGE$_2$, for example, is useful in place of or in combination with less than usual amounts of these known smooth muscle stimulators, for example, to relieve the symptons of paralytic ileus or to control or prevent uterine bleeding after abortion or delivery, to aid in expulsion of the placenta, and during the puerperium. For the latter purpose, the PGE compound is administered by intravenous infusion immediately after abortion or delivery at a dose in the range about 0.01 to about 50 µg. per kg. of body weight per minute until the desired effect is obtained. Subsequent doses are given by intravenous, subcutaneous, or intramuscular injection or infusion during puerperium in the range of 0.01 to 2 mg. per kg. of body weight per day, the exact dose depending on the age, weight, and condition of the patient or animal.

The PGE, PGFβ and PGA compounds are useful as hypotensive agents to reduce blood pressure in mammals including man. For this purpose, the compounds are administered by intravenous infusion at the rate about 0.01 to about 50 µg. per kg. of body weight per minute, or in a single or multiple doses of about 25 to 2500 µg. per kg. of body weight total per day.

The PGE, PGFα, and PGFβ compounds are useful in place of oxytoxin to induce labor in pregnant female animals, including man, cows, sheep, pigs, at or near term or in pregnant animals with intrauterine death of the fetus from about 20 weeks to term. For this purpose, the compound is infused intravenously at a dose 0.01 to 50 µg. per kg. of body weight per minute until or near the termination of the second stage of labor, i.e., expulsion of the fetus. These compounds are especially useful when the female is 1 or more weeks post-mature and natural labor has not started, or 12 to 60 hours after the membranes have ruptured and natural labor has not yet started.

The PGE, PGFα, and PGFβ compounds are useful for controlling the reproductive cycle in ovulating female mammals, including humans and other animals. For that purpose, PGF$_2$α, for example, is administered systemically at a dose level in the range of 0.01 mg. to about 20 mg. per kg. of body weight, advantageously during a span of time starting approximately at the time of ovulation and ending approximately at the time of menses or just prior to menses. Additionally, expulsion of an embryo or fetus is accomplished by similar administration of the compound during the first third or the second third of the normal mammalian gestation period. Accordingly they are useful as abortifacients. They are also useful for induction of menses during approximately the first 2 weeks of a missed menstrual period and accordingly are useful as contraceptive anti-fertility agents.

The PGA compounds and derivatives and salts thereof increase the flow of blood in the mammalian kidney, thereby increasing volume and electrolyte content of the urine. for that reason, PGA compounds are useful in managin cases of renal disfunction, especially in cases of several impaired renal blood flow, for example, the hepatorena syndrome and early kidney transplant rejection. In case of excessive or inappropriate ADH (antidiuretic hormone vasopressin) secretion, the diuretic effect of these compounds is even greater. In anephretic states, the vasopressin action of these compounds is especially useful. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusion of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate a wet dressing for topical application to second and/or third degree burns of skin area 5 to 25 square centimeters would advantageously involve use of an isotonic aqueous solution containing 1 to 500 µg./ml. of the PGB compound or several times that concentration of the PGE compound. Especially for topical use, these prostaglandins are useful in combination with antibiotics, for example, gentamycin, neomycin, polymyxin B, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone.

The novel compounds of this invention induce the biological responses described hereinabove as associated with its particular prostaglandins type. These novel compounds are accordingly useful for the above-described corresponding purposes in the same manner as described above.

The novel PGE, PGFβ and PGA compounds of this invention are also useful as bronchodilators for the treatment of asthma and chronic bronchitis; as such they may be conveniently administered by inhalation of aerosol sprays prepared in a dose range of about 10 µg. to about 10 mg. per ml. of a pharmacologically suitable liquid vehicle.

In addition certain of the novel compounds of this invention are useful for the preparation of other novel compounds of this invention.

The compounds of this invention are also useful as inhibitors of gastric acid secretion and peptic ulcer formation and may be used for the treatment of gastric hyperacidity, gastric erosion, and peptic ulcer. Inhibition of basal gastric acid secretion can be determined by the following procedure.

Female Sprague-Dawley rats weighin 140–160 grams are fasted in individual cages for 18–24 hours. The rats are then lightly anesthetized with ether and their front teeth extracted to avoid destruction of the plastic cannula. A midline incision is then made and the stomach and duodenum exposed. A flanged polyvinyl tube is inserted into the fundic portion of the stomach and secured with a purse string suture line using 4-0 Mersilene. The rat is then dosed by injection of the compound into the duodenum (1.0 ml. per 100 gram body weight). After dosing, the abdominal wall and skin are closed using metal wound clips. The rat is replaced in a cage containing a longitudinal slit to allow the polyvinyl tube to hand freely. An 8 ml. plastic collecting tube is attached to the flanged cannula and hangs freely below the cage. The first 30 minute sample is discarded designating this time as zero. The collecting tube is attached again and samples removed at the end of 60 and 120 minutes. The hourly samples are then transferred to a 15 ml. centrifuged for 5–10 minutes. Total and sediment volume are then recorded with the supernatant volume being used as volume of secretion. A 1 ml. or less aliquot is then removed and placed in a 50 ml. breaker containing 10 ml. of distilled water. This sample is then titrated using 0.01N NaOH to pH 7.0 using a Beckman zeromatic pH meter. Volume, titratable acidity (meq/L) and total acid output (ueq/hour) are recorded. Percent inhibition is determined by comparison with the appropriate control. Groups of these rats were used for preliminary testing, and groups of six rats were used for dose-response evaluations. All compounds are administered in a vehicle consisting of 0.5% methocel, 0.4% tween 80, and saline at a constant volume of 1 ml./100 gram rat. Samples are dispersed by sonification. Percent inhibition is calculated on basis of concurrent vehicle control.

In Table A which follows is given the effect on total acid output after 60 minutes (response A) and 120 minutes (response B) for various doses of representative compounds of this invention.

TABLE A

Inhibition of Gastric Acid Secretion in the Acute Gastric Fistula Rat

|  | Dose mg./kg. | % inhibition of total acid output | |
|---|---|---|---|
|  |  | After 60 minutes | After 120 minutes |
| trans-2-(6-carboxyhexyl)-3-(1-hydroxyoctyl)cyclopentanone | 10[a] | 29 | 78 |
| 2α-(6-carboxyhex-2-cis-enyl)-3β-(1-hydroxyoctyl)-4-hydroxycyclopentanone | 10[a] | 81 | 20 |
| 2β-(6-carboxyhex-2-cis-enyl)-3β-(1-hydroxyoctyl)-4-hydroxycyclopentanone | 10[a] | 100 | 94 |
| 2β-(6-carboxyhex-2-cis-enyl)3β-(1-hydroxyoctyl)-4-hydroxycyclopentanone | 10[b] | 1 | 56 |

[a]intraduodenal route of administration
[b]oral route of administration

The invention will be described in greater detail in conjunction with the following specific examples.

EXAMPLE 1

Preparation of trans-2-(6-carboxyhexyl)-3-(1-hydroxyoctyl)cyclopentanone

A mixture of 18.4 g. (0.0875 mol) of 2-(6-carboxyhexyl)cyclopent-2-en-1-one and 3.75 g. of benzophenone is dissolved in 260 ml. of 1-octanol. The solution is placed in a Pyrex tube and is flushed with nitrogen. The solution is then irradiated in a Rayonet Reactor (Model MGR-100) using a 3500A light source for 4 days. The solution is then mixed with 150 ml. of hexane and a solution of 8.0 g. of sodium hydroxide in 300 ml. of water. The mixture is stirred for 20 minutes. The aqueous layer is separated and the organic layer is washed with 100 ml. of water. The combined aqueous solutions are then washed three times with ether. The aqueous solution is then acidified with hydrochloric acid. The mixture is extracted with ether. The ether solution is washed with a saturated solution of sodium chloride and then dried over magnesium sulfate. The solvent is removed and the residue (26.5 g.) is chromatographed on a dry column of silica gel eluting with benzene-ethylacetate 2:1 containing 0.5% acetic acid to give a fraction containing 11.2 g. (0.033 mol) of trans-2-(6-carboxyhexyl)-3-(1-hydroxyoctyl)cyclopentanone as a mixture of two isomers.

NMR: $\delta_{TMS}^{CDCl_3}$ 6.73 (bs, 2H, OH), 3.70 (m, 1H, C$\underline{H}$OH), 2.31 (t, 2H, C$\underline{H}_2$CO$_2$H), 2.45–1.10 (m's, 28H, alkyl), 0.90 (m, 3H, terminal methyl).

IR: neat, 3455 (OH, 1730 (carbonyls) cm$^{-1}$.

MS: 340 (M+), 322 (M—H$_2$O) m/e.

The two isomers can be separated by thin layer chromatography on silica gel using a solvent mixture consisting of ethyl acetate-benzene 2:3, 1% acetic acid.

EXAMPLES 2–60

In the manner of the preceding Example 1, the various cyclopentenones of Table I are prepared from the cyclopentenone and alcohol shown.

Table I

| Example | Alcohol | Cyclopentenone | Product Cyclopentanone |
|---|---|---|---|
| 2 | methanol | 2-(6-carboxyhexyl)-cyclopent-2-en-1-one | trans-2-(6-carboxyhexyl)-3-(hydroxymethyl)cyclopentanone |
| 3 | 1-heptanol | 2-(6-carboxyhexyl)-cyclopent-2-en-1-one | trans-2-(6-carboxyhexyl)-3-(1-hydroxyheptyl)cyclopentanone |
| 4 | 2-nonanol | 2-(6-carboxyhexyl)-cyclopent-2-en-1-one | trans-2-(6-carboxyhexyl)-3-(1-hydroxy-1-methyloctyl)cyclopentanone |

Table I-continued

| Example | Alcohol | Cyclopentenone | Product Cyclopentanone |
|---|---|---|---|
| 5 | 3-decanol | 2-(6-carboxyhexyl)-cyclopent-2-en-1-one | trans-2-(6-carboxyhexyl)-3-(1-hydroxy-1-ethyloctyl)cyclopentanone |
| 6 | 1-pentanol | 2-(6-carboxyhexyl)-cyclopent-2-en-1-one | trans-2-(6-carboxyhexyl)-3-(1-hydroxypentyl)cyclopentanone |
| 7 | 4-decanol | 2-(6-carboxyhexyl)-cyclopent-2-en-1-one | trans-2-(6-carboxyhexyl)-3-(1-hydroxy-1-propylheptyl)cyclopentanone |
| 8 | 2-octanol | 2-(6-carboxyhexyl)-cyclopent-2-en-1-one | trans-2-(6-carboxyhexyl)-3-(1-hydroxy-1-methylheptyl)cyclopentanone |
| 9 | 2-methyl-1-heptanol | 2-(6-carboxyhexyl)-cyclopent-2-en-1-one | trans-2-(6-carboxyhexyl)-3-(1-hydroxy-2-methylheptyl)cyclopentanone |
| 10 | 2-methyl-1-octanol | 2-(6-carboxyhexyl)-cyclopent-2-en-1-one | trans-2-(6-carboxyhexyl)-3-(1-hydroxy-2-methyloctyl)cyclopentanone |
| 11 | 1-octanol | 2-(5-carboxypentyl)-cyclopent-2-en-1-one | trans-2-(5-carboxypentyl)-3-(1-hydroxyoctyl)cyclopentanone |
| 12 | methanol | 2-(5-carboxypentyl)-cyclopent-2-en-1-one | trans-2-(5-carboxypentyl)-3-(hydroxymethyl)cyclopentanone |
| 13 | 3-decanol | 2-(5-carboxypentyl)-cyclopent-2-en-1-one | trans-2-(5-carboxypentyl)-3-(1-hydroxy-1-ehtyloctyl)cyclopentanone |
| 14 | 2-octanol | 2-(5-carboxypentyl)-cyclopent-2-en-1-one | trans-2-(5-carboxypentyl)-3-(1-hydroxy-1-methylheptyl)cyclopentanone |
| 15 | 2-nonanol | 2-(5-carboxypentyl)-cyclopent-2-en-1-one | trans-2-(5-carboxypentyl)-3-(1-hydroxy-1-methyloctyl)cyclopentanone |
| 16 | 1-octanol | 2-(7-carboxyheptyl)-cyclopent-2-en-1-one | trans-2-(7-carboxyheptyl)-3-(1-hydroxyoctyl)cyclopentanone |
| 17 | methanol | 2-(7-carboxyheptyl)-cyclopent-2-en-1-one | trans-2-(7-carboxyheptyl)-3-(hydroxymethyl)cyclopentanone |
| 18 | 1-heptanol | 2-(7-carboxyheptyl)-cyclopent-2-en-1-one | trans-2-(7-carboxyheptyl)-3-(1-hydroxyheptyl)cyclopentanone |
| 19 | 1-nonanol | 2-(7-carboxyheptyl)-cyclopent-2-en-1-one | trans-2-(7-carboxyheptyl)-3-(1-hydroxynonyl)cyclopentanone |
| 20 | 2-methyl-1-heptanol | 2-(7-carboxyheptyl)-cyclopent-2-en-1-one | trans-2-(7-carboxyheptyl)-3-(1-hydroxy-2-methylheptyl)cyclopentanone |
| 21 | 1-octanol | 2-(6-carboxyhex-2-cis-enyl)cyclopent-2-en-1-one | trans-2-(6-carboxyhex-2-cis-enyl)-3-(1-hydroxyoctyl)cyclopentanone |
| 22 | methanol | 2-(6-carboxyhex-2-cis-enyl)cyclopent-2-en-1-one | trans-2-(6-carboxyhex-2-cis-enyl)-3-(hydroxymethyl)cyclopentanone |
| 23 | 1-nonanol | 2-(6-carboxyhex-2-cis-enyl)cyclopent-2-en-1-one | trans-2-(6-carboxyhex-2-cis-enyl)-3-(1-hydroxynonyl)cyclopentanone |
| 24 | 1-heptanol | 2-(6-carboxyhex-2-cis-enyl)cyclopent-2-en-1-one | trans-2-(6-carboxyhex-2-cis-enyl)-3-(1-hydroxyheptyl)cyclopentanone |
| 25 | 2-nonanol | 2-(6-carboxyhex-2-cis-enyl)cyclopent-2-en-1-one | trans-2-(6-carboxyhex-2-cis-enyl)-3-(1-hydroxy-1-methyloctyl)cyclopentanone |
| 26 | 1-octanol | 2-(7-carboxyhept-2-cis-enyl)cyclopent-2-en-1-one | trans-2-(7-carboxyhept-2-cis-enyl)-3-(1-hydroxyoctyl)cyclopentanone |
| 27 | methanol | 2-(7-carboxyhept-2-cis-enyl)cyclopent-2-en-1-one | trans-2-(7-carboxyhept-2-cis-enyl)-3-(hydroxymethyl)cyclopentanone |
| 28 | 1-decanol | 2-(7-carboxyhept-2-cis-enyl)cyclopent-2-en-1-one | trans-2-(7-carboxyhept-2-cis-enyl)-3-(1-hydroxydecyl)cyclopentanone |
| 29 | 1-pentanol | 2-(7-carboxyhept-2-cis-enyl)cyclopent-2-en-1-one | trans-2-(7-carboxyhept-2-cis-enyl)-3-(1-hydroxypentyl)cyclopentanone |
| 30 | 2-ethyl-1-hexanol | 2-(7-carboxyhept-2-cis-enyl)cyclopent-2-en-1-one | trans-2-(7-carboxyhept-2-cis-enyl)-3-(1-hydroxy-2-ethylhexyl)cyclopentanone |
| 31 | 1-octanol | 2-(6-carboxyhex-4-methyl-2-cis-enyl)-cyclopent-2-en-1-one | trans-2-(6-carboxyhex-4-methyl-2-cis-enyl)-3-(1-hydroxyoctyl)cyclopentanone |
| 32 | methanol | 2-(6-carboxyhex-4-methyl-2-cis-enyl)-cyclopent-2-en-1-one | trans-2-(6-carboxyhex-4-methyl-2-cis-enyl)-3-(hydroxymethyl)cyclopentanone |
| 33 | 1-nonanol | 2-(6-carboxyhex-4-methyl-2-cis-enyl)-cyclopent-2-en-1-one | trans-2-(6-carboxyhex-4-methyl-2-cis-enyl)-3-(1-hydroxynonyl)cyclopentanone |
| 34 | 1-octanol | 2-(6-carboxyhex-4-ethyl-2-cis-enyl)-cyclopent-2-en-1-one | trans-2-(6-carboxyhex-4-ethyl-2-cis-enyl)-3-(1-hydroxyoctyl)cyclopentanone |
| 35 | methanol | 2-(6-carboxyhex-4-ethyl-2-cis-enyl)-cyclopent-2-en-1-one | trans-2-(6-carboxylhex-4-ethyl-2-cis-enyl)-3-(hydroxymethyl)cyclopentanone |
| 36 | 1-octanol | 2-(6-carboxy-5-oxa-hexyl)cyclopent-2-en-1-one | trans-2-(6-carboxy-5-oxahexyl)-3-(1-hydroxyoctyl)cyclopentanone |
| 37 | methanol | 2-(6-carboxy-5-oxa-hexyl)cyclopent-2-en-1-one | trans-2-(6-carboxy-5-oxahexyl)-3-(hydroxymethyl)cyclopentanone |
| 38 | 1-nonanol | 2-(6-carboxy-5-oxa-hexyl)cyclopent-2-en-1-one | trans-2-(6-carboxy-5-oxahexyl)-3-(1-hydroxynonyl)cyclopentanone |
| 39 | 2-nonanol | 2-(6-carboxy-5-oxa-hexyl)cyclopent-2-en-1-one | trans-2-(6-carboxy-5-oxahexyl)-3-(1-hydroxy-1-methyloctyl)cyclopentanone |
| 40 | 4-decanol | 2-(6-carboxy-5-oxa-hexyl)cyclopent-2-en-1-one | trans-2-(6-carboxy-5-oxahexyl)-3-(1-hydroxy-1-propylheptyl)cyclopentanone |
| 41 | 1-octanol | 2-(6-carboxy-5-thia- | trans-2-(6-carboxy-5-thiahexyl)-3-(1-hy- |

Table I-continued

| Example | Alcohol | Cyclopentenone | Product Cyclopentanone |
|---|---|---|---|
| | | hexyl)cyclopent-2-en-1-one | droxyoctyl)cyclopentanone |
| 42 | methanol | 2-(6-carboxy-5-thiahexyl)cyclopent-2-en-1-one | trans-2-(6-carboxy-5-thiahexyl)-3-(hydroxymethyl)cyclopentanone |
| 43 | 2-methyl-1-heptanol | 2-(6-carboxy-5-thiahexyl)cyclopent-2-en-1-one | trans-2-(6-carboxy-5-thiahexyl)-3-(1-hydroxy-2-methylheptyl)cyclopentanone |
| 44 | 4-decanol | 2-(6-carboxy-5-thiahexyl)cyclopent-2-en-1-one | trans-2-(6-carboxy-5-thiahexyl)-3-(1-hydroxy-1-propylheptyl)cyclopentanone |
| 45 | 2-nonanol | 2-(6-carboxy-5-thiahexyl)cyclopent-2-en-1-one | trans-2-(6-carboxy-5-thiahexyl)-3-(1-hydroxy-1-methyloctyl)cyclopentanone |
| 46 | 1-octanol | 2-(6-carboxy-5,5-dimethylhexyl)cyclopent-2-en-1-one | trans-2-(6-carboxy-5,5-dimethylhexyl)-3--1(1-hydroxyoctyl)cyclopentanone |
| 47 | methanol | 2-(6-carboxy-5,5-dimethylhexyl)cyclopent-2-en-1-one | trans-2-(6-carboxy-5,5-dimethylhexyl)-3--(hydroxymethyl)cyclopentanone |
| 48 | 1-nonanol | 2-(6-carboxy-5,5-dimethylhexyl)cyclopent-2-en-1-one | trans-2-(6-carboxy-5,5-dimethylhexyl)-3--(1-hydroxynonyl)cyclopentanone |
| 49 | 2-heptanol | 2-(6-carboxy-5,5-dimethylhexyl)cyclopent-2-en-1-one | trans-2-(6-carboxy-5,5-dimethylhexyl)-3--(1-hydroxy-1-methylhexyl)cyclopentanone |
| 50 | 1-decanol | 2-(6-carboxy-5,5-dimethylhexyl)cyclopent-2-en-1-one | trans-2-(6-carboxy-5,5-dimethylhexyl)-3--(1-hydroxydecyl)cyclopentanone |
| 51 | 1-octanol | 2-(6-carboxy-6-methylhexyl)cyclopent-2-en-1-one | trans-2-(6-carboxy-6-methylhexyl)-3-(1-hydroxyoctyl)cyclopentanone |
| 52 | methanol | 2-(6-carboxy-6-methylhexyl)cyclopent-2-en-1-one | trans-2-(6-carboxy-6-methylhexyl)-3-(hydroxymethyl)cyclopentanone |
| 53 | 2-propanol | 2-(6-carboxy-6-methylhexyl)cyclopent-2-en-1-one | trans-2-(6-carboxy-6-methylhexyl)-3-(1--hydroxy-1-methylethyl)cyclopentanone |
| 54 | 2-octanol | 2-(6-carboxy-6-methylhexyl)cyclopent-2-en-1-one | trans-2-(6-carboxy-6-methylhexyl)-3-(1--hydroxy-1-methylheptyl)cyclopentanone |
| 55 | 3-decanol | 2-(6-carboxy-6-methylhexyl)cyclopent-2-en-1-one | trans-2-(6-carboxy-6-methylhexyl)-3-(1--hydroxy-1-ethyloctyl)cyclopentanone |
| 56 | 1-octanol | 2-(6-carboxy-6-ethylhexyl)cyclopent-2-en-1-one | trans-2-(6-carboxy-6-ethylhexyl)-3-(1--hydroxoctyl)cyclopentanone |
| 57 | methanol | 2-(6-carboxy-6-ethylhexyl)cyclopent-2-en-1-one | trans-2-(6-carboxy-6-ethylhexyl)-3-(hydroxymethyl)cyclopentanone |
| 58 | 2-methyl-1-heptanol | 2-(6-carboxy-6-ethylhexyl)cyclopent-2-en-1-one | trans-2-(6-carboxy-6-ethylhexyl)-3-(1--hydroxy-2-methylheptyl)cyclopentanone |
| 59 | 2-ethyl-1-hexanol | 2-(6-carboxy-6-ethylhexyl)cyclopent-2-en-1-one | trans-2-(6-carboxy-6-ethylhexyl)-3-(1--hydroxy-2-ethylhexyl)cyclopentanone |
| 60 | 1-nonanol | 2-(6-carboxy-6-ethylhexyl)cyclopent-2-en-1-one | trans-2-(6-carboxy-6-ethylhexyl)-3-(1--hydroxynonyl)cyclopentanone |

EXAMPLE 61

Preparation of 2-(6-carboxyhex-2-cis-enyl)-3-(1-hydroxyoctyl)-4-hydroxycyclopentanones A solution of 5.4 g. (0.024 mol) of 2-(6-carboxyhex-2-cis-enyl)-4-hydroxycyclopent-2-en-1-one and 1.47 g. of benzophenone in 100 ml. of 1-octanol is flushed with nitrogen and sealed in a Pyrex tube. The solution is irradiated using a Rayonet Reactor (model MGR-100) and a 3500A light source for ⅔ hour. The reaction mixture is then poured into a solution of 9 g. of sodium bicarbonate in 130 ml. of water which was cooled to 0° C. The mixture is then stirred vigorously at 0° for 15 minutes and 130 ml. of hexane is added. The organic layer is separated and discarded. The aqueous layer is washed three times with ether. The aqueous solution is acidified with hydrochloric acid at 0° and then extracted with ether. The ether solution is washed three times with water and once with a saturated solution of sodium chloride. The ether solution is dried over magnesium sulfate. The ether is removed and the residue (5.8 g.) is chromatographed on a 5 ft. × 3 in. dry column of silica gel eluting with ether containing 0.5% of acetic acid. Two bands are collected. The band with greatest Rf gives 0.5 g. of an oil which is identified as a 2β-(6-carboxyhex-2-cis-enyl)-3β-(1-hydroxyoctyl)-4-hydroxycyclopentanone isomer.

NMR: $\delta_{TMS}^{CDCl_3}$, 5.65 (bs, 3H, OH's), 5.44 (m, 2H, vinyl), 4.63 (m, 1H, ring C$\underline{H}$OH), 3.87 (m, 1H, chain C$\underline{H}$OH), 2.92–1.00 (m's 24H, alkyl), 0.90 (m, 3H, terminal methyl).

IR: neat, 1710, 1730 cm$^{-1}$.

The band with lower Rf gives 2.01 g. of an oil which is shown to be a mixture of a 2β-(6-carboxyhex-2-cis-enyl)-3β-(1-hydroxyoctyl)-4-hydroxycyclopentanone isomer and 2α-(6-carboxyhex-2-cis-enyl)-3β-(1-hydroxyoctyl)-4-hydroxycyclopentanone isomers.

NMR: $\delta_{TMS}^{CDCl_3}$, 6.01 (bs, 3H, OH's), 5.43 (m, 2H, vinyl), 4.47 (m, 1H, ring C$\underline{H}$OH), 4.10–3.57 (m's, 1H, chain C$\underline{H}$OH), 2.96–1.10 (m's, 24H, alkyl), 0.90 (m, 3H, terminal methyl).

IR: neat, 1710, 1725 (sh) cm$^{-1}$.

When a sample of the 2β-(6-carboxyhex-2-cis-enyl)-3β-(1-hydroxyoctyl)-4-hydroxycyclopentanone is treated with potassium carbonate in methanol for a brief period, it is epimerized to a 2α-(6-carboxyhex-2-cis-enyl)-3β-(1-hydroxyoctyl)-4-hydroxycyclopentanone isomer.

EXAMPLES 62–126

In the manner of the preceding Example 61, the following 2α,3β-4-hydroxycyclopentanones are prepared from the indicated cyclopentenones and alcohols. Also formed, though not listed in Table II, are the corresponding 2β,3β-4-hydroxycyclopentanones also claimed in this invention.

Table II

| Example | Alcohol | Cyclopentanone | Product |
| --- | --- | --- | --- |
| 62 | 1-nonanol | 2-(6-carboxyhex-2-cis-enyl)-4-hydroxycyclopent-2-en-1-one | 2α-(6-carboxyhex-2-cis-enyl)-3β-(1-hydroxynonyl)-4-hydroxycyclopentanone |
| 63 | methanol | 2-(6-carboxyhex-2-cis-enyl)-4-hydroxycyclopent-2-en-1-one | 2α-(6-carboxyhex-2-cis-enyl)-3β-(hydroxymethyl)-4-hydroxycyclopentanone |
| 64 | 1-decanol | 2-(6-carboxyhex-2-cis-enyl)-4-hydroxycyclopent-2-en-1-one | 2α-(6-carboxyhex-2-cis-enyl)-3β-(1-hydroxydecyl)-4-hydroxycyclopentanone |
| 65 | 1-pentanol | 2-(6-carboxyhex-2-cis-enyl)-4-hydroxycyclopent-2-en-1-one | 2α-(6-carboxyhex-2-cis-enyl)-3β-(1-hydroxypentyl)-4-hydroxycyclopentanone |
| 66 | 3-decanol | 2-(6-carboxyhex-2-cis-enyl)-4-hydroxycyclopent-2-en-1-one | 2α-(6-carboxyhex-2-cis-enyl)-3β-(1-hydroxy-1-ethyloctyl)-4-hydroxycyclopentanone |
| 67 | 2-decanol | 2-(6-carboxyhex-2-cis-enyl)-4-hydroxycyclopent-2-en-1-one | 2α-(6-carboxyhex-2-cis-enyl)-3β-(hydroxy-1-methylnonyl)-4-hydroxycyclopentanone |
| 68 | 2-ethyl-1-hexanol | 2-(6-carboxyhex-2-cis-enyl)-4-hydroxycyclopent-2-en-1-one | 2α-(6-carboxyhex-2-cis-enyl)-3β-(1-hydroxy-2-ethylhexyl)-4-hydroxycyclopentanone |
| 69 | 2-methyl-1-heptanol | 2-(6-carboxyhex-2-cis-enyl)-4-hydroxycyclopent-2-en-1-one | 2α-(6-carboxyhex-2-cis-enyl)-3β-(1-hydroxy-2-methylheptyl)-4-hydroxycyclopentanone |
| 70 | 2-methyl-1-octanol | 2-(6-carboxyhex-2-cis-enyl)-4-hydroxycyclopent-2-en-1-one | 2α-(6-carboxyhex-2-cis-enyl)-3β-(1-hydroxy-2-methyloctyl)-4-hydroxycyclopentanone |
| 71 | 4-decanol | 2-(6-carboxyhex-2-cis-enyl)-4-hydroxycyclopent-2-en-1-one | 2α-(6-carboxyhex-2-cis-enyl)-3β-(1-hydroxy-1-propylheptyl)-4-hydroxycyclopentanone |
| 72 | 1-octanol | 2-(7-carboxyhept-2-cis-enyl)-4-hydroxycyclopent-2-en-1-one | 2α-(7-carboxyhept-2-cis-enyl)-3β-(1-hydroxyoctyl)-4-hydroxycyclopentanone |
| 73 | methanol | 2-(7-carboxyhept-2-cis-enyl)-4-hydroxycyclopent-2-en-1-one | 2α-(7-carboxyhept-2-cis-enyl)-3β-(hydroxymethyl)-4-hydroxycyclopentanone |
| 74 | 2-decanol | 2-(7-carboxyhept-2-cis-enyl)-4-hydroxycyclopent-2-en-1-one | 2α-(7-carboxyhept-2-cis-enyl)-3β-(1-hydroxy-1methylnonyl)-4-hydroxycyclopentanone |
| 75 | 3-decanol | 2-(7-carboxyhept-2-cis-enyl)-4-hydroxycyclopent-2-en-1-one | 2α-(7-carboxyhept-2-cis-enyl)-3β-(1-hydroxy-1-ethyloctyl)-4-hydroxycyclopentanone |
| 76 | 2-nonanol | 2-(7-carboxyhept-2-cis-enyl)-4-hydroxycyclopent-2-en-1-one | 2α-(7-carboxyhept-2-cis-enyl)-3β-(1-hydroxy-1-methyloctyl)-4-hydroxycyclopentanone |
| 77 | 1-octanol | 2-(5-carboxypentyl)-4-hydroxycyclopent-2-en-1-one | 2α-(5-carboxypentyl)-3β-(1-hydroxyoctyl)-4-hydroxycyclopentanone |
| 78 | methanol | 2-(5-carboxypentyl)-4-hydroxycyclopent-2-en-1-one | 2α-(5-carboxypentyl)-3β-(hydroxymethyl)-4-hydroxycyclopentanone |
| 79 | 1-heptanol | 2-(5-carboxypentyl)-4-hydroxycyclopent-2-en-1-one | 2α-(5-carboxypentyl)-3β-(1-hydroxyheptyl)-4-hydroxycyclopentanone |
| 80 | 1-nonanol | 2-(5-carboxypentyl)-4-hydroxycyclopent-2-en-1-one | 2α-(5-carboxypentyl)-3β-(1-hydroxynonyl)-4-hydroxycyclopentanone |
| 81 | 2-heptanol | 2-(5-carboxypentyl)-4-hydroxycyclopent-2-en-1-one | 2α-(5-carboxypentyl)-3β-(1-hydroxy-1-methylhexyl)-4-hydroxycyclopentanone |
| 82 | 1-octanol | 2-(7-carboxyheptyl)-4-hydroxycyclopent-2-en-1-one | 2α-(7-carboxyheptyl)-3β-(1-hydroxyoctyl)-4-hydroxycyclopentanone |
| 83 | methanol | 2-(7-carboxyheptyl)-4-hydroxycyclopent-2-en-1-one | 2α-(7-carboxyheptyl)-3β-(hydroxymethyl)-4-hydroxycyclopentanone |
| 84 | 1-decanol | 2-(7-carboxyheptyl)-4-hydroxycyclopent-2-en-1-one | 2α-(7-carboxypentyl)-3β-(1-hydroxydecyl)-4-hydroxycyclopentanone |
| 85 | 1-pentanol | 2-(7-carboxyheptyl)-4-hydroxycyclopent-2-en-1-one | 2α-(7-carboxypentyl)-3β-(1-hydroxypentyl)-4-hydroxycyclopentanone |
| 86 | 2-nonanol | 2-(7-carboxyheptyl)-4-hydroxycyclopent-2-en-1-one | 2α-(7-carboxypentyl)-3β-(1-hydroxy-1-methyloctyl)-4-hydroxycyclopentanone |
| 87 | 1-octanol | 2-(8-carboxyoctyl)-4-hydroxycyclopent-2-en-1-one | 2α-(8-carboxyoctyl)-3β-(1-hydroxyoctyl)-4-hydroxycyclopentanone |
| 88 | methanol | 2-(8-carboxyoctyl)-4-hydroxycyclopent-2-en-1-one | 2α-(8-carboxyoctyl)-3β-(hydroxymethyl)-4-hydroxycyclopentanone |

Table II-continued

| Example | Alcohol | Cyclopentanone | Product |
| --- | --- | --- | --- |
| 89 | 1-heptanol | 2-(8-carboxyoctyl)-4-hydroxycyclopent-2-en-1-one | 2α-(8-carboxyoctyl)-3β-(1-hydroxyheptyl)-4-hydroxycyclopentanone |
| 90 | 2-ethyl-1-hexanol | 2-(8-carboxyoctyl)-4-hydroxycyclopent-2-en-1-one | 2α-(8-carboxyoctyl)-3β-(1-hydroxy-2-ethylhexyl)-4-hydroxycyclopentanone |
| 91 | 4-decanol | 2-(8-carboxyoctyl)-4-hydroxycyclopent-2-en-1-one | 2α-(8-carboxyoctyl)-3β-(1-hydroxy-1-propylheptyl)-4-hydroxycyclopentanone |
| 92 | 1-octanol | 2-(6-carboxyhexyl)-4-hydroxycyclopent-2-en-1-one | 2α-(6-carboxyhexyl)-3β-(1-hydroxyoctyl)-4-hydroxycyclopentanone |
| 93 | methanol | 2-(6-carboxyhexyl)-4-hydroxycyclopent-2-en-1-one | 2α-(6-carboxyhexyl)-3β-(hydroxymethyl)-4-hydroxycyclopentanone |
| 94 | 2-decanol | 2-(6-carboxyhexyl)-4-hydroxycyclopent-2-en-1-one | 2α-(6-carboxyhexyl)-3β-(1-hydroxy-1-methylnonyl)-4-hydroxycyclopentanone |
| 95 | 2-methyl-1-octanol | 2-(6-carboxyhexyl)-4-hydroxycyclopent-2-en-1-one | 2α-(6-carboxyhexyl)-3β-(1-hydroxy-2-methyloctyl)-4-hydroxycyclopentanone |
| 96 | 2-nonanol | 2-(6-carboxyhexyl)-4-hydroxycyclopent-2-en-1-one | 2α-(6-carboxyhexyl)-3β-(1-hydroxy-1-methyloctyl)-4-hydroxycyclopentanone |
| 97 | 1-octanol | 2-(6-carboxy-4-methylhex-2-cis-enyl)-4-hydroxycyclopent-2-en-1-one | 2α-(6-carboxy-4-methylhex-2-cis-enyl)-3β-(1-hydroxyoctyl)-4-hydroxycyclopentanone |
| 98 | methanol | 2-(6-carboxy-4-methylhex-2-cis-enyl)-4-hydroxycyclopent-2-en-1-one | 2α-(6-carboxy-4-methylhex-2-cis-enyl)-3β-(hydroxymethyl)-4-hydroxycyclopentanone |
| 99 | 3-decanol | 2-(6-carboxy-4-methylhex-2-cis-enyl)-4-hydroxycyclopent-2-en-1-one | 2α-(6-carboxy-4-methylhex-2-cis-enyl)-3β-(1-hydroxy-1-ethyloctyl)-4-hydroxycyclopentanone |
| 100 | 1-octanol | 2-(6-carboxy-4-ethylhex-2-cis-enyl)-4-hydroxycyclopent-2-en-1-one | 2α-(6-carboxy-4-ethylhex-2-cis-enyl)-3β-(1-hydroxyoctyl)-4-hydroxycyclopentanone |
| 101 | methanol | 2-(6-carboxy-4-ethylhex-2-cis-enyl)-4-hydroxycyclopent-2-en-1-one | 2α-(6-carboxy-4-ethylhex-2-cis-enyl)-3β-(hydroxymethyl)-4-hydroxycyclopentanone |
| 102 | 1-octanol | 2-(6-carboxy-5-oxahexyl)-4-hydroxycyclopent-2-en-1-one | 2α-(6-carboxy-5-oxahexyl)-3β-(1-hydroxyoctyl)-4-hydroxycyclopentanone |
| 103 | methanol | 2-(6-carboxy-5-oxahexyl)-4-hydroxycyclopent-2-en-1-one | 2α-(6-carboxy-5-oxahexyl)-3β-(hydroxymethyl)-4-hydroxycyclopentanone |
| 104 | 1-nonanol | 2-(6-carboxy-5-oxahexyl)-4-hydroxycyclopent-2-en-1-one | 2α-(6-carboxy-5-oxahexyl)-3β-(1-hydroxynonyl)-4-hydroxycyclopentanone |
| 105 | 1-heptanol | 2-(6-carboxy-5-oxahexyl)-4-hydroxycyclopent-2-en-1-one | 2α-(6-carboxy-5-oxahexyl)-3β-(1-hydroxyheptyl)-4-hydroxycyclopentanone |
| 106 | 2-octanol | 2-(6-carboxy-5-oxahexyl)-4-hydroxycyclopent-2-en-1-one | 2α-(6-carboxy-5-oxahexyl)-3β-(1-hydroxy-1-methylheptyl)-4-hydroxycyclopentanone |
| 107 | 1-octanol | 2-(6-carboxy-5-thiahexyl)-4-hydroxycyclopent-2-en-1-one | 2α-(6-carboxy-5-thiahexyl)-3β-(1-hydroxyoctyl)-4-hydroxycyclopentanone |
| 108 | methanol | 2-(6-carboxy-5-thiahexyl)-4-hydroxycyclopent-2-en-1-one | 2α-(6-carboxy-5-thiahexyl)-3β-(hydroxymethyl)-4-hydroxycyclopentanone |
| 109 | 1-decanol | 2-(6-carboxy-5-thiahexyl)-4-hydroxycyclopent-2-en-1-one | 2α-(6-carboxy-5-thiahexyl)-3β-(1-hydroxydecyl)-4-hydroxycyclopentanone |
| 110 | ethanol | 2-(6-carboxy-5-thiahexyl)-4-hydroxycyclopent-2-en-1-one | 2α-(6-carboxy-5-thiahexyl)-3β-(1-hydroxyethyl)-4-hydroxycyclopentanone |
| 111 | 2-nonanol | 2-(6-carboxy-5-thiahexyl)-4-hydroxycyclopent-2-en-1-one | 2α-(6-carboxy-5-thiahexyl)-3β-(1-hydroxy-1-methyloctyl)-4-hydroxycyclopentanone |
| 112 | 1-octanol | 2-(6-carboxy-5,5-dimethylhexyl)-4-hydroxycyclopent-2-en-1-one | 2α-(6-carboxy-5,5-dimethylhexyl)-3β-(1-hydroxyoctyl)-4-hydroxycyclopentanone |
| 113 | methanol | 2-(6-carboxy-5,5-dimethylhexyl)-4-hydroxycyclopent-2-en-1-one | 2α-(6-carboxy-5,5-dimethylhexyl)-3β-(hydroxymethyl)-4-hydroxycyclopentanone |
| 114 | 1-decanol | 2-(6-carboxy-5,5-dimethylhexyl)-4-hydroxycyclopent-2-en-1-one | 2α-(6-carboxy-5,5-dimethylhexyl)-3β-(1-hydroxydecyl)-4-hydroxycyclopentanone |
| 115 | 1-nonanol | 2-(6-carboxy-5,5-dimethylhexyl)-4-hydroxycyclopent-2-en-1-one | 2α-(6-carboxy-5,5-dimethylhexyl)-3β-(1-hydroxynonyl)-4-hydroxycyclopentanone |
| 116 | 1-heptanol | 2-(6-carboxy-5,5-dimethylhexyl)-4-hydroxycyclopent-2-en-1-one | 2α-(6-carboxy-5,5-dimethylhexyl)-3β-(1-hydroxyheptyl)-4-hydroxycyclopentanone |
| 117 | 1-octanol | 2-(6-carboxy-6-methylhexyl)-4-hydroxycyclopent-2-en-1-one | 2α-(6-carboxy-6-methylhexyl)-3β-(1-hydroxyoctyl)-4-hydroxycyclopentanone |
| 118 | methanol | 2-(6-carboxy-6-methyl- | 2α-(6-carboxy-6-methylhexyl)-3β-(hy- |

Table II-continued

| Example | Alcohol | Cyclopentanone | Product |
|---|---|---|---|
| | | hexyl)-4-hydroxycyclopent-2-en-1-one | droxymethyl)-4-hydroxycyclopentanone |
| 119 | 1-nonanol | 2-(6-carboxy-6-methylhexyl)-4-hydroxycyclopent-2-en-1-one | 2α-(6-carboxy-6-methylhexyl)-3β-(1-hydroxynonyl)-4-hydroxycyclopentanone |
| 120 | 2-nonanol | 2-(6-carboxy-6-methylhexyl)-4-hydroxycyclopent-2-en-1-one | 2α-(6-carboxy-6-methylhexyl)-3β-(1-hydroxy-1-methyloctyl)-4-hydroxycyclopentanone |
| 121 | 2-methyl-1-heptanol | 2-(6-carboxy-6-methylhexyl)-4-hydroxycyclopent-2-en-1-one | 2α-(6-carboxy-6-methylhexyl)-3β-(1-hydroxy-2-methylheptyl)-4-hydroxycyclopentanone |
| 122 | 1-octanol | 2-(6-carboxy-6-ethylhexyl)-4-hydroxycyclopent-2-en-1-one | 2α-(6-carboxy-6-ethylhexyl)-3β-(1-hydroxyoctyl)-4-hydroxycyclopentanone |
| 123 | methanol | 2-(6-carboxy-6-ethylhexyl)-4-hydroxycyclopent-2-en-1-one | 2α-(6-carboxy-6-ethylhexyl)-3β-(hydroxymethyl)-4-hydroxycyclopentanone |
| 124 | 2-heptanol | 2-(6-carboxy-6-ethylhexyl)-4-hydroxycyclopent-2-en-1-one | 2α-(6-carboxy-6-ethylhexyl)-3β-(1-hydroxy-1-methylhexyl)-4-hydroxycyclopentanone |
| 125 | 2-methyl-1-octanol | 2-(6-carboxy-6-ethylhexyl)-4-hydroxycyclopent-2-en-1-one | 2α-(6-carboxy-6-ethylhexyl)-3β-(1-hydroxy-2-methyloctyl)-4-hydroxycyclopentanone |
| 126 | 3-decanol | 2-(6-carboxy-6-ethylhexyl)-4-hydroxycyclopent-2-en-1-one | 2α-(6-carboxy-6-ethylhexyl)-3β-(1-hydroxy-1-ethyloctyl)-4-hydroxycyclopentanone |

EXAMPLE 127

Preparation of trans-2-(6-carboxyhex-2-cis-enyl)-3-(1-hydroxy-octyl)-cyclopent-4-en-1-one A solution of 0.4 g. (1.12 mmol.) of 2-(6-carboxyhex-2-cis-enyl)-3-(1-hydroxyoctyl)-4-hydroxycyclopentanone as a mixture of isomers in 15 ml. of tetrahydrofuran containing 8 ml. of 1.5N hydrochloric acid is allowed to stand at room temperature under a nitrogen atmosphere for 2 days. The mixture is poured into water and extracted with ether. The ether solution is washed with a saturated solution of sodium chloride and dried over magnesium sulfate. The solvent is removed and the residue was chromatographed on three 2000 mu. silica gel plates developing with ethyl acetate:benzene 1:1 containing 2% acetate acid. From the major band is isolated 0.325 g. of trans-2-(6-carboxyhex-2-cis-enyl)-3-(1-hydroxyoctyl)-cyclopent-4-en-1-one as a mixture of two isomers.

NMR $\delta_{tms}$, $^{CDCl_3}$ 7.72 and 7.60 (dd's, 1H, vinyl β to carbonyl in each isomer, J = 2.2, J = 6.0 Hz), 7.67 (bs, 2H, OH's), 6.24 (m, 1H, vinyl α to carbonyl), 5.42 (m, 2H, vinyl), 3.72 (m, 1H, CHOH), 2.77 (m, 1H, ring allylic proton), 2.55–1.90 (m's, 7H, allylic, α to carbonyl). 1.90–1.10 (m, 16H, alkyl), 0.90 (m, 3H, terminal $CH_3$).

IR: neat, 3330, 1707, 1585 cm$^{-1}$.

EXAMPLES 128–181

In the manner of the preceding Example 127, the following cyclopentenones were prepared as shown in Table III.

Table III

| Example | Starting 4-Hydroxy cyclopentanone of Example | Product cyclopent-4-en-1-one |
|---|---|---|
| 128 | 62 | trans-2-(6-carboxyhex-2-cis-enyl)-3-(1-hydroxynonyl)cyclopent-4-en-one |
| 129 | 63 | trans-2-(6-carboxyhex-2-cis-enyl)-3-(hydroxymethyl)cyclopent-4-en-1-one |
| 130 | 64 | trans-2-(6-carboxyhex-2-cis-enyl)-3-(1-hydroxydecyl)cyclopent-4-en-1-one |
| 131 | 65 | trans-2-(6-carboxyhex-2-cis-enyl)-3-(1-hydroxypentyl)cyclopent-4-en-1-one |
| 132 | 66 | trans-2-(6-carboxyhex-2-cis-enyl)-3-(1-hydroxy-1-ethyloctyl)cyclopent-4-en-1-one |
| 133 | 67 | trans-2-(6-carboxyhex-2-cis-enyl)-3-(1-hydroxy-1-methylnonyl)cyclopent-4-en-1-one |
| 134 | 68 | trans-2-(6-carboxyhex-2-cis-enyl)-3-(1-hydroxy-2-ethylhexyl)cyclopent-4-en-1-one |
| 135 | 69 | trans-2-(6-carboxyhex-2-cis-enyl)-3-(1-hydroxy-2-methylheptyl)cyclopent-4-en-1-one |
| 136 | 70 | trans-2-(6-carboxyhex-2-cis-enyl)-3-(1-hydroxy-2-methyloctyl)cyclopent-4-en-1-one |
| 137 | 71 | trans-2-(6-carboxyhex-2-cis-enyl)-3-(1-hydroxy-1-propylheptyl)cyclopent-4-en-1-one |
| 138 | 72 | trans-2-(7-carboxyhept-2-cis-enyl)-3-(1-hydroxyoctyl)cyclopent-4-en-1-one |
| 139 | 73 | trans-2-(7-carboxyhept-2-cis-enyl)-3-(hydroxymethyl)cyclopent-4-en-1-one |
| 140 | 75 | trans-2-(7-carboxyhept-2-cis-enyl)-3-(1-hydroxy-1-ethyloctyl)cyclopent-4-en-1-one |
| 141 | 77 | trans-2-(5-carboxypentyl)-3-(1-hydroxyoctyl)cyclopent-4-en-1-one |
| 142 | 78 | trans-2-(5-carboxypentyl)-3-(hydroxymethyl)cyclopent-4-en-1-one |
| 143 | 80 | trans-2-(5-carboxypentyl)-3-(1-hydroxynonyl)cyclopent-4-en-1-one |
| 144 | 82 | trans-2-(7-carboxyheptyl)-3-(1-hydroxyoctyl)cyclopent-4-en-1-one |
| 145 | 83 | trans-2-(7-carboxyheptyl)-3-(hydroxymethyl)cyclopent-4-en- |

Table III-continued

| Example | Starting 4-Hydroxy cyclopentanone of Example | Product cyclopent-4-en-1-one |
|---|---|---|
| 146 | 86 | trans-2-(7-carboxyheptyl)-3-(1-hydroxy-1-methyloctyl)cyclopent-4-en-1-one |
| 147 | 87 | trans-2-(8-carboxyoctyl)-3-(1-hydroxyoctyl)cyclopent-4-en-1-one |
| 148 | 88 | trans-2-(8-carboxyoctyl)-3-(hydroxymethyl)cyclopent-4-en-1-one |
| 149 | 91 | trans-2-(8-carboxyheptyl)-3-(1-hydroxy-1-propylheptyl)cyclopent-4-en-1-one |
| 150 | 92 | trans-2-(6-carboxyhexyl)-3-(1-hydroxyoctyl)cyclopent-4-en-1-one |
| 151 | 93 | trans-2-(6-carboxyhexyl)-3-(hydroxymethyl)cyclopent-4-en-1-one |
| 152 | 94 | trans-2-(6-carboxyheptyl)-3-(1-hydroxy-1-methylnonyl)cyclopent-4-en-1-one |
| 153 | 95 | trans-2-(6-carboxyhexyl)-3-(1-hydroxy-2-methyloctyl)cyclopent-4-en-1-one |
| 154 | 96 | trans-2-(6-carboxyhexyl)-3-(1-hydroxy-1-methyloctyl)cyclopent-4-1-one |
| 155 | 97 | trans-2-(6-carboxy-4-methylhex-2-cis-enyl)-3-(1-hydroxyoctyl)cyclopent-4-en-1-one |
| 156 | 98 | trans-2-(6-carboxy-4-methylhex-2-cis-enyl)-3-(hydroxymethyl)cyclopent-4-en-1-one |
| 157 | 99 | trans-2-(6-carboxy-4-methylhex-2-cis-enyl)-3-(1-hydroxy-1-ethyloctyl)cyclopent-4-en-1-one |
| 158 | 100 | trans-2-(6-carboxy-4-ethylhex-2-cis-enyl)-3-(1-hydroxyoctyl)cyclopent-4-en-1-one |
| 159 | 101 | trans-2-(6-carboxy-4-ethylhex-2-cis-enyl)-3-(hydroxymethyl)cyclopent-4-en-1-one |
| 160 | 102 | trans-2-(6-carboxy-5-oxahexyl)-3-(1-hydroxyoctyl)cyclopent-4-en-1-one |
| 161 | 103 | trans-2-(6-carboxy-5-oxahexyl)-3-(hydroxymethyl)cyclopent-4-en-1-one |
| 162 | 104 | trans-2-(6-carboxy-5-oxahexyl)-3-(1-hydroxynonyl)cyclopent-4-en-1-one |
| 163 | 105 | trans-2-(6-carboxy-5-oxahexyl)-3-(1-hydroxyheptyl)cyclopent-4-en-1-one |
| 164 | 107 | trans-2-(6-carboxy-5-thiahexyl)-3-(1-hydroxyoctyl)cyclopent-4-en-1-one |
| 165 | 108 | trans-2-(6-carboxy-5-thiahexyl)-3-(hydroxymethyl)cyclopent-4-en-1-one |
| 166 | 109 | trans-2-(6-carboxy-5-thiahexyl)-3-(1-hydroxydecyl)cyclopent-4-en-1-one |
| 167 | 111 | trans-2-(6-carboxy-5-thiahexyl)-3-(1-hydroxy-1-methyloctyl)cyclopent-4-en-1-one |
| 168 | 112 | trans-2-(6-carboxy-5,5-dimethylhexyl)-3-(1-hydroxyoctyl)cyclopent-4-en-1-one |
| 169 | 113 | trans-2-(6-carboxy-5,5-dimethylhexyl)-3-(hydroxymethyl)cyclopent-4-en-1-one |
| 170 | 115 | trans-2-(6-carboxy-5,5-dimethylhexyl)-3-(1-hydroxynonyl)cyclopent-4-en-1-one |
| 171 | 116 | trans-2-(6-carboxy-5,5-dimethylhexyl)-3-(1-hydroxyheptyl)cyclopent-4-en-1-one |
| 172 | 117 | trans-2-(6-carboxy-6-methylhexyl)-3-(1-hydroxyoctyl)cyclopent-4-en-1-one |
| 173 | 118 | trans-2-(6-carboxy-6-methylhexyl)-3-(hydroxymethyl)cyclopent-4-en-1-one |
| 174 | 119 | trans-2-(6-carboxy-6-methylhexyl)-3-(1-hydroxynonyl)cyclopent-4-en-1-one |
| 175 | 120 | trans-2-(6-carboxy-6-methylhexyl)-3-(1-hydroxy-1-methyloctyl)cyclopent-4-en-1-one |
| 176 | 121 | trans-2-(6-carboxy-6-methylhexyl)-3-(1-hydroxy-2-methylheptyl)cyclopent-4-en-1-one |
| 177 | 122 | trans-2-(6-carboxy-6-ethylhexyl)-3-(1-hydroxyoctyl)cyclopent-4-en-1-one |
| 178 | 123 | trans-2-(6-carboxy-6-ethylhexyl)-3-(hydroxymethyl)cyclopent-4-en-1-one |
| 179 | 124 | trans-2-(6-carboxy-6-ethylhexyl)-3-(1-hydroxy-1-methylhexyl)cyclopent-4-en-1-one |
| 180 | 125 | trans-2-(6-carboxy-6-ethylhexyl)-3-(1-hydroxy-2-methyloctyl)cyclopent-4-en-1-one |
| 181 | 126 | trans-2-(6-carboxy-6-ethylhexyl)-3-(1-hydroxy-1-ethyloctyl)cyclopent-4-en-1-one |

EXAMPLE 182

Preparation of 2α-(6-carboxyhexyl)-3β-(1-hydroxyoctyl)cyclopentan-1α-ol and 1β-ol To a solution of 0.5 g. (1.47 mmol) of trans-2-(6-carboxyhexyl)-3-(1-hydroxyoctyl)cyclopentanone as a mixture of two isomers in 10 ml. of 95% ethanol is added with stirring in small portions 0.4 g. of sodium borohydride. The mixture is allowed to stir for 1 hour. The mixture is poured into water and carefully acidifed with hydrochloric acid. The mixture is extracted with ether. The ether solution is dried over magnesium sulfate. The solvent is removed giving 0.48 g. of 2α-(6-carboxyhexyl)-3β-(1-hydroxyoctyl)cyclopentanol as a mixture of 1α and 1β-ols.

NMR: $\delta_{TMS}^{CDCl_3}$, 5.57 (bs, 3H, OH's), 4.28, 3.92 (m's, 1H, ring C$\underline{H}$OH), 3.60 (m, 1H, chain C$\underline{H}$OH), 2.32 (t, 2H, C$\underline{H}_2$CO$_2$H), 2.10–1.00 (m, 31H, alkyl), 0.90 (m, 3H, terminal methyl).

MS: 324 (M—H$_2$O), 306 (M—2H$_2$O) m/e.
IR: neat, 3370, 1710 cm$^{-1}$.

EXAMPLE 183-232

In the manner of the preceding Example 182, the following cyclopentanol (mixtures of 1α and 1β-ols), separable by chromatography are prepared as shown in Table IV.

Table IV

| Example | Cyclopentanone of Example | Product cyclopentanol |
|---|---|---|
| 183 | 2 | 2α-(6-carboxyhexyl)-3β-(hydroxymethyl)cyclopentanol |
| 184 | 3 | 2α-(6-carboxyhexyl)-3β-(1-hydroxyheptyl)cyclopentanol |
| 185 | 4 | 2α-(6-carboxyhexyl)-3β-(1-hydroxy-1-methyloctyl)cyclopentanol |
| 186 | 5 | 2α-(6-carboxyhexyl)-3β-(1-hydroxy-1-ethyloctyl)cyclopentanol |
| 187 | 6 | 2α-(6-carboxyhexyl)-3β-(1-hydroxypentyl)cyclopentanol |
| 188 | 7 | 2α-(6-carboxyhexyl)-3β-(1-hydroxy-1-propylheptyl)cyclopentanol |
| 189 | 8 | 2α-(6-carboxyhexyl)-3β-(1-hydroxy-1-methylheptyl)cyclopentanol |
| 190 | 9 | 2α-(6-carboxyhexyl)-3β-(1-hydroxy-2-methylheptyl)cyclopentanol |
| 191 | 10 | 2α-(6-carboxyhexyl)-3β-(1-hydroxy-2-methyloctyl)cyclopentanol |
| 192 | 11 | 2α-(5-carboxypentyl)-3β-(1-hydroxyoctyl)cyclopentanol |
| 193 | 12 | 2α-(5-carboxypentyl)-3β-(hydroxymethyl)cyclopentanol |
| 194 | 14 | 2α-(5-carboxypentyl)-3β-(1-hydroxy-1-methylheptyl)cyclopentanol |
| 195 | 15 | 2α-5-carboxypentyl)-3β-(1-hydroxy-1-methyloctyl)cyclopentanol |
| 196 | 16 | 2α-(7-carboxyheptyl)-3β-(1-hydroxyoctyl)cyclopentanol |
| 197 | 17 | 2α-(7-carboxyheptyl)-3β-(hydroxymethyl)cyclopentanol |
| 198 | 18 | 2α-(7-carboxyheptyl)-3β-(1-hydroxyheptyl)cyclopentanol |
| 199 | 19 | 2α-(7-carboxyheptyl)-3β-(1-hydroxynonyl)cyclopentanol |
| 200 | 21 | 2α-(6-carboxyhex-2-cis-enyl)-3β-(1-hydroxyoctyl)cyclopentanol |
| 201 | 23 | 2α-(6-carboxyhex-2-cis-enyl)-3β-(1-hydroxynonyl)cyclopentanol |
| 202 | 25 | 2α-(6-carboxyhex-2-cis-enyl)-3β-(1-hydroxy-1-methyloctyl)cyclopentanol |
| 203 | 26 | 2α-(7-carboxyhept-2-cis-enyl)-3β-(1-hydroxyoctyl)cyclopentanol |
| 204 | 27 | 2α-(7-carboxyhept-2-cis-enyl)-3β-(hydroxymethyl)cyclopentanol |
| 205 | 31 | 2α-(6-carboxyhex-4-methyl-2-cis-enyl)-3β-(1-hydroxyoctyl)cyclopentanol |
| 206 | 33 | 2α-(6-carboxyhex-4-methyl-2-cis-enyl)-3β-(1-hydroxynonyl)cyclopentanol |
| 207 | 34 | 2α-(6-carboxy-4-ethyl-2-cis-enyl)-3β-(1-hydroxyoctyl)cyclopentanol |
| 208 | 36 | 2α-(6-carboxy-5-oxahexyl)-3β-(1-hydroxyoctyl)cyclopentanol |
| 209 | 39 | 2α-(6-carboxy-5-oxahexyl)-3β-(1-hydroxy-1-methyloctyl)cyclopentanol |
| 210 | 41 | 2α-(6-carboxy-5-thiahexyl)-3β-(1-hydroxyoctyl)cyclopentanol |
| 211 | 42 | 2α-(6-carboxy-5-thiahexyl)-3β-(1-hydroxymethyl)cyclopentanol |
| 212 | 44 | 2α-(6-carboxy-5-thiahexyl)-3β-(1-hydroxy-1-propylheptyl)cyclopentanol |
| 213 | 46 | 2α-(6-carboxy-5,5-dimethylhexyl)-3-β-(1-hydroxyoctyl)cyclopentanol |
| 214 | 48 | 2α-(6-carboxy-5,5-dimethylhexyl)-3β-(1-hydroxynonyl)cyclopentanol |
| 215 | 51 | 2α-(6-carboxy-6-methylhexyl)-3β-(1-hydroxyoctyl)cyclopentanol |
| 216 | 55 | 2α-(6-carboxy-6-methylhexyl)-3β-(1-hydroxy-1-ethyloctyl)cyclopentanol |
| 217 | 56 | 2α-(6-carboxy-6-ethylhexyl)-3β-(1-hydroxyoctyl)cyclopentanol |
| 218 | 60 | 2α-(6-carboxy-6-ethylhexyl)-3β-(1-hydroxynonyl)cyclopentanol |
| 219 | 61 | 2α-(6-carboxyhex-2-cis-enyl)-3β-(1-hydroxyoctyl)cyclopentan-1,4-diol |
| 220 | 63 | 2α-(6-carboxyhex-2-cis-enyl)-3β-(hydroxymethyl)cyclopentan-1,4-diol |
| 221 | 67 | 2α-(6-carboxyhex-2-cis-enyl)-3β-(1-hydroxy-1-methylnonyl)cyclopentan-1,4-diol |
| 222 | 75 | 2α-(7-carboxyhept-2-cis-enyl)-3β-(1-hydroxy-1-ethyloctyl)cyclopentan-1,4-diol |
| 223 | 92 | 2α-(6-carboxyhexyl)-3β-(1-hydroxyoctyl)cyclopentan-1,4-diol |
| 224 | 96 | 2α-(6-carboxyhexyl)-3β-(1-hydroxy-1-methyloctyl)cyclopentan-1,4-diol |
| 225 | 102 | 2α-(6-carboxy-5-oxahexyl)-3β-(1-hydroxyoctyl)cyclopentan-1,4-diol |
| 226 | 105 | 2α-(6-carboxy-5-oxahexyl)-3β-(1-hydroxyheptyl)cyclopentan-1,4-diol |
| 227 | 107 | 2α-(6-carboxy-5-thiahexyl)-3β-(1-hydroxyoctyl)cyclopentan-1,4-diol |
| 228 | 111 | 2α-(6-carboxy-5-thiahexyl)-3β-(1-hydroxy-1-methyloctyl)cyclopentan-1,4-diol |
| 229 | 112 | 2α-(6-carboxy-5,5-dimethylhexyl)-3β-(1-hydroxyoctyl)cyclopentan-1,4-diol |
| 230 | 117 | 2α-(6-carboxy-6-methylhexyl)-3β-(1-hydroxyoctyl)cyclopentan-1,4-diol |
| 231 | 122 | 2α-(6-carboxy-6-ethylhexyl)-3β-(1-hydroxyoctyl)cyclo- |

Table IV-continued

| Example | Cyclopentanone of Example | Product cyclopentanol |
|---|---|---|
| 232 | 123 | pentan-1,4-diol<br>2α-(6-carboxy-6-ethylhexyl)-3β-(hydroxymethyl)cyclopentan-1,4-diol |

EXAMPLE 233

Preparation of 2-(6-carboxyhex-2-cis-enyl)-3-(1-hydroxyoctyl)cyclopentan-1,4-diols To a solution of 0.5 g. (1.41 mmol) of a mixture of isomers of 2-(6-carboxyhex-2-cis-enyl)-3-(1-hydroxyoctyl)-4-hydroxycyclopentanone in 20 ml. of tetrahydrofuran is added at −20° C. under nitrogen with stirring 7.3 ml. of 0.5M tetrahydrofuran solution of lithium perhydro-9b-boraphenalylhydride (3.67 mmol). The solution is allowed to warm up to 5° C. over a 1 hour period. To the solution is added a solution of 0.3 g. of sodium hydroxide in 5 ml. of water followed by 2 ml. of 30% hydrogen peroxide. After brief stirring the mixture is poured into water. The water layer is washed with ether and then acidifed with hydrochloric acid. The mixture is extracted with ether. The ether solution is dried over magnesium sulfate. The ether is removed leaving 0.52 g. of 2-(6-carboxyhex-2-cis-enyl)-3-(1-hydroxyoctyl)cyclopentan-1,4-diol as a mixture of isomers.

NMR: $\delta_{TMS}^{CDCL_3}$, 5.55 (m, 6H, vinyl + OH's), 4.00–4.10 (m, 2H, ring CHOH's), 3.94–3.50 (m, 1H, chain CHOH), 2.55–1.10 (m's, 24H, alkyl), 0.90 (m, 3H, terminal $CH_3$)

IR: neat, 3340, 1710 $cm^{-1}$.

MS: 338 (m—$H_2O$), 320 (m—$2H_2O$) m/e.

EXAMPLES 234–282

Although the reduction described in Example 233 was conducted on a mixture os isomers, the reduction can also be performed on the separated 2α, 3β and the 2β, 3β isomers. In Table V is shown the conversion of various 2α, 3β-4-hydroxycyclopentanones to 2α,3β-cyclopentan-1,4-diols using the procedure of Example 233. The reduction of the corresponding 2α,3β-4-hydroxycyclopentanones is also accomplished in a like manner to give the corresponding 2β,3β-cyclopentan-1,4-diols also claimed in this invention.

TABLE V

| Example | 4-Hydroxycyclopentanone of Example | Product |
|---|---|---|
| 234 | 64 | 2α-(6-carboxyhex-2-cis-enyl)-3β-(1-hydroxydecyl)cyclopentan-1,4-diol |
| 235 | 65 | 2α-(6-carboxyhex-2-cis-enyl)-3β-(1-hydroxypentyl)cyclopentan-1,4-diol |
| 236 | 66 | 2α-(6-carboxyhex-2-cis-enyl)-3β-(1-hydroxy-1-ethyloctyl)-cyclopentan-1,4-diol |
| 237 | 67 | 2α-(6-carboxyhex-2-cis-enyl)-3β-(1-hydroxy-1-methylnonyl)cyclopentan-1,4-diol |
| 238 | 70 | 2α-(6-carboxyhex-2-cis-enyl)-3β-(1-hydroxy-2-methyloctyl)cyclopentan-1,4-diol |
| 239 | 71 | 2α-(6-carboxyhex-2-cis-enyl)-3β-(1-hydroxy-1-propylheptyl)cyclopentan-1,4-diol |
| 240 | 72 | 2α-(7-carboxyhept-2-cis-enyl)-3β-(1-hydroxyoctyl)cyclopentan-1,4-diol |
| 241 | 73 | 2α-(7-carboxyhept-2-cis-enyl)-3β-(hydroxymethyl)cyclopentan-1,4-diol |
| 242 | 77 | 2α-(5-carboxypentyl)-3β-(1-hydroxyoctyl)cyclopentan-1,4-diol |
| 243 | 80 | 2α-(5-carboxypentyl)-3β-(1-hydroxynonyl)cyclopent-1,4-diol |
| 244 | 81 | 2α-(5-carboxypentyl)-3β-(1-hydroxy-1-methylhexyl)cyclopentan-1,4-diol |
| 245 | 82 | 2α-(7-carboxyheptyl)-3β-(1-hydroxyoctyl)cyclopentan-1,4-diol |
| 246 | 83 | 2α-(7-carboxyheptyl)-3β-(hydroxymethyl)cyclopentan-1,4-diol |
| 247 | 86 | 2α-(7-carboxyheptyl)-3β-(1-hydroxy-1-methyloctyl)cyclopentan-1,4-diol |
| 248 | 87 | 2α-(8-carboxyoctyl)-3β-(hydroxyoctyl)cyclopentan-1,4-diol |
| 249 | 89 | 2α-(8-carboxyoctyl)-3β-(1-hydroxyheptyl)cyclopentan-1,4-diol |
| 250 | 91 | 2α-(8-carboxyoctyl)-3β-(1-hydroxy-1-propylheptyl)cyclopentan-1,4-diol |
| 251 | 92 | 2α-(6-carboxyhexyl)-3β-(hydroxyoctyl)cyclopentan-1,4-diol |
| 252 | 93 | 2α-(6-carboxyhexyl)-3β-(hydroxymethyl)cyclopentan-1,4-diol |
| 253 | 94 | 2α-(6-carboxyhexyl)-3β-(1-hydroxy-1-methylnonyl)cyclopentan-1,4-diol |
| 254 | 95 | 2α-(6-carboxyhexyl)-3β-(1-hydroxy-2-methyloctyl)cyclopentan-1,4-diol |
| 255 | 96 | 2α-(6-carboxyhexyl)-3β-(1-hydroxy-1-methyloctyl)cyclopentan-1,4-diol |
| 256 | 97 | 2α-(6-carboxy-4-methylhex-2-cis-enyl)-3β-(1-hydroxyoctyl)cyclopentan-1,4-diol |
| 257 | 99 | 2α-(6-carboxy-4-methylhex-2-cis-enyl)-3β-(1-hydroxy-1-ethyloctyl)cyclopentan-1,4-diol |
| 258 | 100 | 2α-(6-carboxy-4-ethylhex-2-cis-enyl)-3β-(1-hydroxyoctyl)cyclopentan-1,4-diol |
| 259 | 101 | 2α-(6-carboxy-4-ethylhex-2-cis-enyl)-3β-(hydroxymethyl)-cyclopentan-1,4-diol |
| 260 | 102 | 2α-(6-carboxy-5-oxahexyl)-3β-(1-hydroxyoctyl)cyclopentan-1,4-diol |

TABLE V-continued

| Example | 4-Hydroxycyclopentanone of Example | Product |
|---|---|---|
| 261 | 103 | 2α-(6-carboxy-5-oxahexyl)-3β-(hydroxymethyl)cyclopentan-1,4-diol |
| 262 | 104 | 2α-(6-carboxy-5-oxahexyl)-3β-(1-hydroxynonyl)cyclopentan-1,4-diol |
| 263 | 105 | 2α-(6-carboxy-5-oxahexyl)-3β-(1-hydroxyheptyl)cyclopentan-1,4-diol |
| 264 | 106 | 2α-(6-carboxy-5-oxahexyl)-3β-(1-hydroxy-1-methylheptyl)-cyclopentan-1,4-diol |
| 265 | 107 | 2α-(6-carboxy-5-thiahexyl)-3β-(1-hydroxyoctyl)cyclopentan-1,4-diol |
| 266 | 108 | 2α-(6-carboxy-5-thiahexyl)-3β-(hydroxymethyl)cyclopentan-1,4-diol |
| 267 | 109 | 2α-(6-carboxy-5-thiahexyl)-3β-(1-hydroxydecyl)cyclopentan-1,4-diol |
| 268 | 111 | 2α-(6-carboxy-5-thiahexyl)-3β-(1-hydroxy-1-methyloctyl)-cyclopentan-1,4-diol |
| 269 | 112 | 2α-(6-carboxy-5,5-dimethylhexyl)-3β-(1-hydroxyoctyl)-cyclopentan-1,4-diol |
| 270 | 113 | 2α-(6-carboxy-5,5-dimethylhexyl)-3β-(hydroxymethyl)-cyclopentan-1,4-diol |
| 271 | 114 | 2α-(6-carboxy-5,5-dimethylhexyl)-3β-(1-hydroxydecyl)-cyclopentan-1,4-diol |
| 272 | 115 | 2α-(6-carboxy-5,5-dimethylhexyl)-3β-(1-hydroxynonyl)-cyclopentan-1,4-diol |
| 273 | 117 | 2α-(6-carboxy-6-methylhexyl)-3β-(1-hydroxyoctyl)cyclopentan-1,4-diol |
| 274 | 118 | 2α-(6-carboxy-6-methylhexyl)-3β -(hydroxymethyl)cyclopentan-1,4-diol |
| 275 | 119 | 2α-(6-carboxy-6-methylhexyl)-3β-(1-hydroxynonyl)cyclopentan-1,4-diol |
| 276 | 120 | 2α-(6-carboxy-6-methylhexyl)-3β-(1-hydroxy-1-methyloctyl)cyclopentan-1,4-diol |
| 277 | 121 | 2α-(6-carboxy-6-methylhexyl)-3β-(1-hydroxy-2-methylheptyl)cyclopentan-1,4-diol |
| 278 | 122 | 2α-(6-carboxy-6-ethylhexyl)-3β-(1-hydroxyoctyl)cyclopentan-1,4-diol |
| 279 | 123 | 2α-(6-carboxy-6-ethylhexyl)-3β-(hydroxymethyl)cyclopentan-1,4-diol |
| 280 | 124 | 2α-(6-carboxy-6-ethylhexyl)-3β-(1-hydroxy-1-methylhexyl)cyclopentan-1,4-diol |
| 281 | 125 | 2α-(6-carboxy-6-ethylhexyl)-3β-(1-hydroxy-2-methyloctyl)cyclopentan-1,4-diol |
| 282 | 126 | 2α-(6-carboxy-6-ethylhexyl)-3β-(1-hydroxy-1-ethyloctyl)-cyclopentan-1,4-diol |

EXAMPLE 283

Preparation of 4-fluorophenoxyacetyl chloride

A solution of 13.0 g. of 4-fluorophenoxyacetic acid and 15 ml. of oxalyl chloride in 80 ml. benzene-15 ml. tetrahydrofuran is stirred 19 hours. The solvent is removed and the residue is distilled (71°–74° C., 0.2 mm) to give 13.1 g. of 4-fluorophenoxyacetyl chloride.

EXAMPLE 284

Preparation of trans-2-(6-carboxyhexyl)-3-(n-hexanoyloxymethyl)cyclopentanone

A mixture of 0.8 g. (3.30 mmol) of trans-2-(6-carboxyhexyl)-3-(hydroxymethyl)cyclopentanone and 0.8 ml. of n-hexanoyl chloride is stirred for 40 minutes. Most of the unreacted hexanoyl chloride is removed at reduced pressure at 50° C. The residue is dissolved in ether and mixed with silica gel, Celite and Norite. The solution is filtered. The solvent is removed. The residue is chromatographed of four 2000 mu silica gel plates using ethyl acetate-benzene 1:1 containing 1.5% acetic acid. The major band at $R_f$ 0.75 was collected to give 0.885 g. of trans-2-(6-carboxyhexyl)-3-(hexanoyloxymethyl)cyclopentanone.

NMR: $\delta_{TMS}^{CDCL_3}$ 9.10 (bs, 1H, CO$_2$H), 4.18 (m, 2H, —CH$_2$O—), 2.50–1.80 (m's, 9H, α to carbonyl, cyclopentyl protons), 1.80–0.9 (m, 19H, alkyl)

IR: neat, 1708, 1731 cm$^{-1}$.

EXAMPLES 285–305

In the manner of Example 283, acid chlorides are prepared from the acids listed below in Table VI; in the manner of Example 284, these acid chlorides are reacted with the indicated alcohols to give the product esters shown.

Table VI

| Example | Alcohol of Example | Carboxylic Acid | Product Ester |
|---|---|---|---|
| 285 | 1 | acetic | trans-2-(6-carboxyhexyl)-3-(1-acetyloxyoctyl)cyclopentanone |
| 286 | 3 | n-butanoic | trans-2-(6-carboxyhexyl)-3-(1-(n-butanoyloxy)heptyl)-cyclopentanone |
| 287 | 2 | p-fluorophenoxy acetic | trans-2-(6-carboxyhexyl)-3-(p-fluorophenoxyacetyl-oxymethyl)cyclopentanone |
| 288 | 11 | n-hexanoic | trans-2-(5-carboxypentyl)-3-(1-(n-hexanoyloxy)octyl)-cyclopentanone |
| 289 | 12 | n-hexanoic | trans-2-(5-carboxypentyl)-3-(n-hexanoyloxymethyl)-cyclopentanone |
| 290 | 17 | m-chlorophenoxy acetic | trans-2-(7-carboxyheptyl)-3-(m-chlorophenoxyacetyl-oxymethyl)cyclopentanone |
| 291 | 21 | n-heptanoic | trans-2-(6-carboxyhex-2-cis-enyl)-3-(1-(n-heptanoyloxy)octyl)cyclopentanone |

Table VI-continued

| Example | Alcohol of Example | Carboxylic Acid | Product Ester |
|---|---|---|---|
| 292 | 22 | n-hexanoic | trans-2-(6-carboxyhex-2-cis-enyl)-3-(n-hexanoyloxymethyl)cyclopentanone |
| 293 | 22 | 3-phenyl propanoic | trans-2-(6-carboxyhex-2-cis-enyl)-3-((3-phenylpropanoyloxy)methyl)cyclopentanone |
| 294 | 22 | m-trifluoromethylphenoxy acetic | trans-2-(6-carboxyhex-2-cis-enyl)-3-(m-trifluoromethylphenoxyacetyloxymethyl)cyclopentanone |
| 295 | 27 | n-octanoic | trans-2-(7-carboxyhept-2-cis-enyl)-3-(n-octanoyloxymethyl)-cyclopentanone |
| 296 | 32 | p-methoxyphenoxy acetic | trans-2-(6-carboxyhex-4-methyl-2-cis-enyl)-3-(p-methoxyphenoxyacetyloxymethyl)cyclopentanone |
| 297 | 36 | acetic | trans-2-(6-carboxy-5-oxahexyl)-3-(1-acetyloxyoctyl)-cyclopentanone |
| 298 | 37 | 2,4-dichlorophenoxy acetic | trans-2-(6-carboxy-5-oxahexyl)-3-(2,4-dichlorophenoxyacetyloxymethyl)cyclopentanone |
| 299 | 42 | n-hexanoic | trans-2-(6-carboxy-5-thiahexyl)-3-(n-hexanoyloxymethyl)cyclopentanone |
| 300 | 47 | n-octanoic | trans-2-(6-carboxy-5 5-dimethylhexyl)-3-(n-octanoyloxymethyl)cyclopentanone |
| 301 | 51 | 3-methylbutanoic | trans-2-(6-carboxy-6-methylhexyl)-3-(1-(3-methylbutanoyloxy)octyl)cyclopentanone |
| 302 | 52 | p-fluorophenoxy acetic | trans-2-(6-carboxy-6-methylhexyl)-3-(p-fluorophenoxyacetyloxymethyl)cyclopentanone |
| 303 | 57 | p-methylphenoxy acetic | trans-2-(6-carboxy-6-ethylhexyl)-3-(p-methylphenoxyacetyloxymethyl)cyclopentanone |
| 304 | 57 | n-pentanoic | trans-2-(6-carboxy-6-ethylhexyl)-3-(n-pentanoyloxymethyl)cyclopentanone |
| 305 | 60 | n-butanoic | trans-2-(6-carboxy-6-ethylhexyl)-3-(1-(n-butanoyloxy)nonyl)cyclopentanone |

EXAMPLE 306

Preparation of trans-2-(6-carbomethoxyhexyl)-3-(1-hydroxyoctyl)cyclopentanone

To a solution of 0.5 g. (1.47 mmol) of trans-2-(6-carboxyhexyl)-3-(1-hydroxyoctyl)cyclopentanone is added on etheral solution of diazomethane until a permanent yellow color remains. The solvent and excess diazomethane are removed un a stream of nitrogen. After removing traces of solvent at reduced pressure, 0.52 g. of trans-2-(6-carbomethoxyhexyl)-3-(1-hydroxyoctyl)-cyclopentanone is obtained.

NMR: $T_{MS},^{CDCl_3}$ 3.65 (S, 3H, OCH$_3$), 3.60 (m, 1H, CHPH), 2.50–0.90 (m's 31H, alkyl)

IR: neat, 3501, 1740 cm$^{-1}$.

EXAMPLES 307–345

In the manner described above for Example 306, the esters in Table VII are prepared from the indicated diazoalkane and carboxylic acid.

Table VII

| Example | Carboxylic Acid of Example | diazoalkane | Product |
|---|---|---|---|
| 307 | 2 | diazoethane | trans-2-(6-carboethoxyhexyl)-3-(hydroxymethyl)cyclopentanone |
| 308 | 13 | diazomethane | trans-2-(5-carbomethoxypentyl)-3-(1-hydroxy-1-ethyloctyl)cyclopentanone |
| 309 | 21 | diazopropane | trans-2-(6-carbopropoxyhex-2-cis-enyl)-3-(1-hydroxyoctyl)cyclopentanone |
| 310 | 33 | diazodecane | trans-2-(carbodecoxyhex-4-methyl-2-cis-enyl)-3-(1-hydroxynonyl)cyclopentanone |
| 311 | 36 | diazobutane | trans-2-(6-carbobutoxy-5-oxahexyl)-3-(1-hydroxyoctyl)cyclopentanone |
| 312 | 41 | diazooctane | trans-2-(6-carbooctoxy-5-thiahexyl)-3-(1-hydroxyoctyl)cyclopentanone |
| 313 | 55 | diazopentane | trans-2-(6-carbopentoxy-6-methylhexyl)-3-(1-hydroxy-1-ethyloctyl)cyclopentanone |
| 314 | 61 | diazomethane | 2α-(6-carbomethoxyhex-2-cis-enyl)-3β-(1-hydroxyoctyl)-4-hydroxycyclopentanone |
| 315 | 63 | diazoethane | 2α-(6-carboethoxyhex-2-cis-enyl)-3β-(hydroxymethyl)-4-hydroxycyclopentanone |
| 316 | 92 | diazooctane | 2α-(6-carbooctoxyhexyl)-3β-(1-hydroxyoctyl)-4-hydroxycyclopentanone |
| 317 | 104 | diazobutane | 2α-(6-carbobutoxy-5-oxahexyl)-3β-(1-hydroxynonyl)-4-hydroxycyclopentanone |
| 318 | 120 | diazodecane | 2α-(6-carbodecoxy-6-methylhexyl)-3β-(1-hydroxy-1-methyloctyl)-4-hydroxycyclopentanone |
| 319 | 127 | diazomethane | trans-2-(6-carbomethoxyhex-2-cis-enyl)-3-(1-hydroxyoctyl)cyclopent-4-en-1-one |
| 320 | 132 | diazoethane | trans-2-(6-carboethoxyhex-2-cis-enyl)-3-(1-hydroxy-1-ethyloctyl)cyclopent-4-en-1-one |
| 321 | 150 | diazopropane | trans-2-(6-carbopropoxyhexyl)-3-(1-hydroxyoctyl)cyclopent-4-en-1-one |
| 322 | 151 | diazoheptane | trans-2-(6-carboheptoxyhexyl)-3-(hydroxymethyl)cyclopent-4-en-1-one |
| 323 | 160 | diazooctane | trans-2-(6-carbooctoxy-5-oxahexyl)-3-(1-hydroxyoctyl)cyclopent-4-en-1-one |
| 324 | 167 | diazononane | trans-2-(6-carbnonoxy-5-thiahexyl)-3-(1-hydroxy-1-1-methyloxtyl)cyclopent-4-en-1-one |
| 325 | 174 | diazomethane | trans-2-(carbomethoxy-6-methylhexyl)-3-(1-hydroxynonyl)cyclopent-4-en-1-one |
| 326 | 182 | diazomethane | 2α-(6-carbomethoxyhexyl)-3β-(1-hydroxyoctyl)cyclopentanol |
| 327 | 185 | diazopropane | 2α-(6-carbopropoxyhexyl)-3β-(1-hydroxy-1-methyloctyl)- |

Table VII-continued

| Example | Carboxylic Acid of Example | diazoalkane | Product |
|---|---|---|---|
| 328 | 196 | diazooctane | 2α-(7-carbooctoxyheptyl)-3β-(1-hydroxyoctyl)-cyclopentanol |
| 329 | 210 | diazodecane | 2α-(6-carbodecoxy-5-thiahexyl)-3β-(1-hydroxyoctane)-cyclopentanol |
| 330 | 200 | diazomethane | 2α-(6-carbomethoxyhex-2-cis-enyl)-3β-(1-hydroxyoctyl)cyclopentanol |
| 331 | 216 | diazoethane | 2α-(6-carboethoxy-6-methylhexyl)-3β-(1-hydroxy-1-ethyloctyl)cyclopentanol |
| 332 | 233 | diazomethane | 2α-(6-carbomethoxyhex-2-cis-enyl)-3β-(1-hydroxyoctyl)cyclopentan-1,4-diol |
| 333 | 237 | diazopropane | 2α-(6-carbopropoxyhex-2-cis-enyl)-3β-(1-hydroxy-1-methylnonyl)cyclopentan-1,4-diol |
| 334 | 245 | diazooctane | 2α-(7-carbooctoxyheptyl)-3β-(1-hydroxyoctyl)cyclopentan-1,4-diol |
| 335 | 251 | diazomethane | 2α-(6-carbomethoxyhexyl)-3β-(1-hydroxyoctyl)cyclopentan-1,4-diol |
| 336 | 261 | diazodecane | 2α-(6-carbodecoxy-5-oxahexyl)-3β-(hydroxymethyl)-cyclopentan-1,4-diol |
| 337 | 275 | diazobutane | 2α-(6-carbobutoxy-6-methylhexyl)-3β-(1-hydroxynonyl)cyclopentan-1,4-diol |
| 338 | 284 | diazoethane | 2α-(6-carboethoxyhexyl)-3-(n-hexanoyloxymethyl)-cyclopentanone |
| 339 | 287 | diazoethane | trans-2-(6-carboethoxyhexyl)-3-(p-fluorophenoxyacetyloxymethyl)cyclopentanone |
| 340 | 291 | diazopentane | trans-2-(6-carbopentoxyhex-2-cis-enyl)-3-(1-(n-heptanoyloxy)octyl)cyclopentanone |
| 341 | 294 | diazobutane | trans-2-(6-carbobutoxyhex-2-cis-enyl)-3-(trifluoromethylphenoxyacetyloxymethyl)cyclopentanone |
| 342 | 299 | diazohexane | trans-2-(6-carbohexoxy-5-thiahexyl)-3-(n-hexanoyloxymethyl)cyclopentanone |
| 343 | 302 | diazomethane | trans-2-(6-carbomethoxy-6-methylhexyl)-3-(p-fluorophenoxyacetyloxymethyl)cyclopentanone |
| 345 | 305 | diazodecane | trans-2-(6-carbodecoxy-6-ethylhexyl)-3-(1-(n-butanoyloxy)nonyl)cyclopentanone |

EXAMPLE 346

Preparation of trans-2-(6-carboxyhexyl)-2-(1-hydroxyoctyl)cyclopentanone p-carboxyphenylhydrazone A mixture of 0.20 g. of trans-2-(6-carboxyhexyl)-3-(1-hydroxyoctyl)cyclopentanone, 0.20 g. of p-carboxyphenylhydrazine and one drop of acetic acid in 20 ml. of ethanol is stirred at 40° C. for 1 hour and then allowed to stand at room temperature for 4 days. The mixture is poured into water and extracted with ether. The ether is removed and the residue is purified by chromatography giving 0.210 g. of trans-2-(6-carboxyhexyl)-3-(1-hydroxyoctyl)cyclopentanone p-carboxyphenylhydrazone.

EXAMPLES 347–360

In the manner of Example 346, the compounds listed in Table VIII are prepared from the indicated cyclopentanone and the indicated nitrogen compounds.

Table VIII

| Example | Cyclopentanone of Example | $R_9$—$NH_2$ | Product |
|---|---|---|---|
| 347 | 1 | hydroxylamine | trans-2-(6-carboxyhexyl)-3-(1-hydroxyoctyl)-cyclopentanone oxime |
| 348 | 1 | methoxylamine | trans-2-(6-carboxyhexyl)-3-(1-hydroxyoctyl)-cyclopentanone methoxime |
| 349 | 1 | semicarbazide | trans-2-(6-carboxyhexyl)-3-(1-hydroxyoctyl)-cyclopentanone semicarbazone |
| 350 | 1 | p-chlorophenyl-hydrazine | trans-2-(6-carboxyhexyl)-3-(1-hydroxyoctyl)-cyclopentanone p-chlorophenylhydrazone |
| 351 | 61-2α,3β isomer | hydroxylamine | 2α-(6-carboxyhex-2-cis-enyl)-3β-(1-hydroxyoctyl)-4-hydroxycyclopentanone oxime |
| 352 | 61-2α,3β isomer | methoxylamine | 2α-(6-carboxyhex-2-cis-enyl)-3β-(1-hydroxyoctyl)-4-hydroxycyclopentanone semicarbazone |
| 353 | 61-2α,3β isomer | semicarbazide | 2α-(6-carboxyhex-2-cis-enyl)-3β-(1-hydroxyoctyl)-4-hydroxycyclopentanone p-chlorophenylhydrazone |
| 354 | 61-2α,3β isomer | p-chlorophenyl-hydrazine | 2α-(6-carboxyhex-2-cis-enyl)-3β-(1-hydroxyoctyl)-4-hydroxycyclopentanone |
| 355 | 61-2α,3β isomer | p-carboxyphenyl-hydrazine | 2α-(6-carboxyhex-2-cis-enyl)-3β-(1-hydroxyoctyl)-4-hydroxycyclopentanone p-carboxyphenylhydrazone |
| 356 | 92 | hydroxylamine | 2α-(6-carboxyhexyl)-3β-(1-hydroxyoctyl)-4-hydroxycyclopentanone oxime |
| 357 | 92 | methoxylamine | 2α-(6-carboxyhexyl)-3β-(1-hydroxyoctyl)-4-hydroxycyclopentanone methoxime |
| 358 | 92 | semicarbazide | 2α-(6-carboxyhexyl)-3β-(1-hydroxyoctyl)-4-hydroxycyclopentanone semicarbazone |
| 359 | 92 | p-chlorophenyl-hydrazide | 2α-(6-carboxyhexyl)-3β-(1-hydroxyoctyl)-4-hydroxycyclopentanone p-chlorophenylhydrazone |
| 360 | 92 | p-carboxyphenyl-hydrazide | 2α-(6-carboxyhexyl)-3β-(1-hydroxyoctyl)-4-hydroxycyclopentanone p-carboxyphenylhydrazone |

I claim:
1. An optically active compound of the formula:

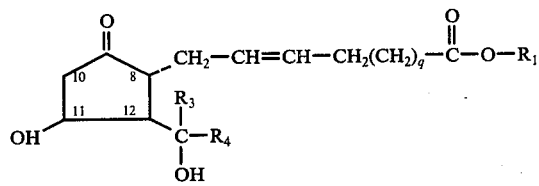

which represents the absolute configuration of the naturally occuring mammalian prostaglandins, or a racemic compound of that formula and the mirror image thereof wherein $R_1$ is selected from the group consisting of hydrogen and $C_1$-$C_6$ alkyl; $R_3$ is selected from the group consisting of hydrogen and $C_1$-$C_3$ alkyl; $R_4$ is selected from the group consisting of hydrogen and $C_1$-$C_{10}$ alkyl; and $q$ is an integer from 1 to 4 inclusive.

2. The compound according to claim 1, l-9-oxo-11α,13α-dihydroxy-5-cis-prostenoic acid.

3. The compound according to claim 1, dl-9-oxo-11α,13α-dihydroxy-5-cis-prostenoic acid.

4. The compound according to claim 1, l-9-oxo-11α,13β-dihydroxy-5-cis-prostenoic acid.

5. The compound according to claim 1, l-9-oxo-11α,13α-dihydroxy prostenoic acid.

6. The compound according to claim 1, l-9-oxo-11α,13-dihydroxy-5-cis-14,15,16,17,18,19,20-heptanor-prostenoic acid.

7. The compound according to claim 1, dl-9-oxo-11α,13-dihydroxy-5-cis-14,15,16,17,18,19,20-heptanor-prostenoic acid.

* * * * *